United States Patent
Karlsson et al.

(12)

(10) Patent No.: US 6,372,955 B1
(45) Date of Patent: Apr. 16, 2002

(54) METHODS FOR PRODUCING B CELLS AND ANTIBODIES FROM H2-O MODIFIED TRANSGENIC MICE

(75) Inventors: Lars Karlsson, La Jolla; Wai-Ping Leung, San Diego; Per A. Peterson, Rancho Santa Fe; Christopher Alfonso, San Diego, all of CA (US)

(73) Assignee: Ortho McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/516,390

(22) Filed: Mar. 1, 2000

Related U.S. Application Data

(63) Continuation-in-part of application No. 09/250,898, filed on Feb. 16, 1999, now abandoned.
(60) Provisional application No. 60/074,847, filed on Feb. 17, 1998.
(51) Int. Cl.⁷ ...................... A01K 67/00; A01K 67/027; C12N 15/00; C12P 21/00
(52) U.S. Cl. ..................... 800/4; 800/5; 800/6; 800/13; 800/14; 800/18
(58) Field of Search .............................. 800/13, 14, 18, 800/4, 5, 6

(56) References Cited

PUBLICATIONS

Alfonso, Christopher; Liljedahl, Monika; Winqvist, Ola; Surh, Charles D.; Peterson, Per A.; Fung–Leung, Wai–Ping; Karlsson, Lars. The role of H2–O and HLA–DO in major histocompatibility complex class II–restricted antigen processing and presentation. Immunological Reviews, vol. 172, 255–266, 1999.

Liljedahl, Monika; Winqvist, Ola; Surh, Charles D.; Wong, Phillip; Ngo, Karen; Teyton, Luc; Peterson, Per A.; Brunmark, Anders; Rudensky, Alexander Y.; Fung–Leung, Wai–Ping; Karlsson, Lars. Altered Antigen Presentation in Mice Lacking H2–O. Immunity, vol. 8, 233–243, Feb., 1998.

*Primary Examiner*—Deborah J. R. Clark
*Assistant Examiner*—Anne-Marie Baker
(74) *Attorney, Agent, or Firm*—John W. Wallen., III

(57) ABSTRACT

A transgenic animal with alterations in an H2-O gene is prepared by introduction of an altered H2-O gene into a host animal. The resulting transgenic animals produce a substantially greater frequency of high affinity antibodies compared to H2-O wild type animals. A method for the production of high affinity antibodies is disclosed.

2 Claims, 17 Drawing Sheets

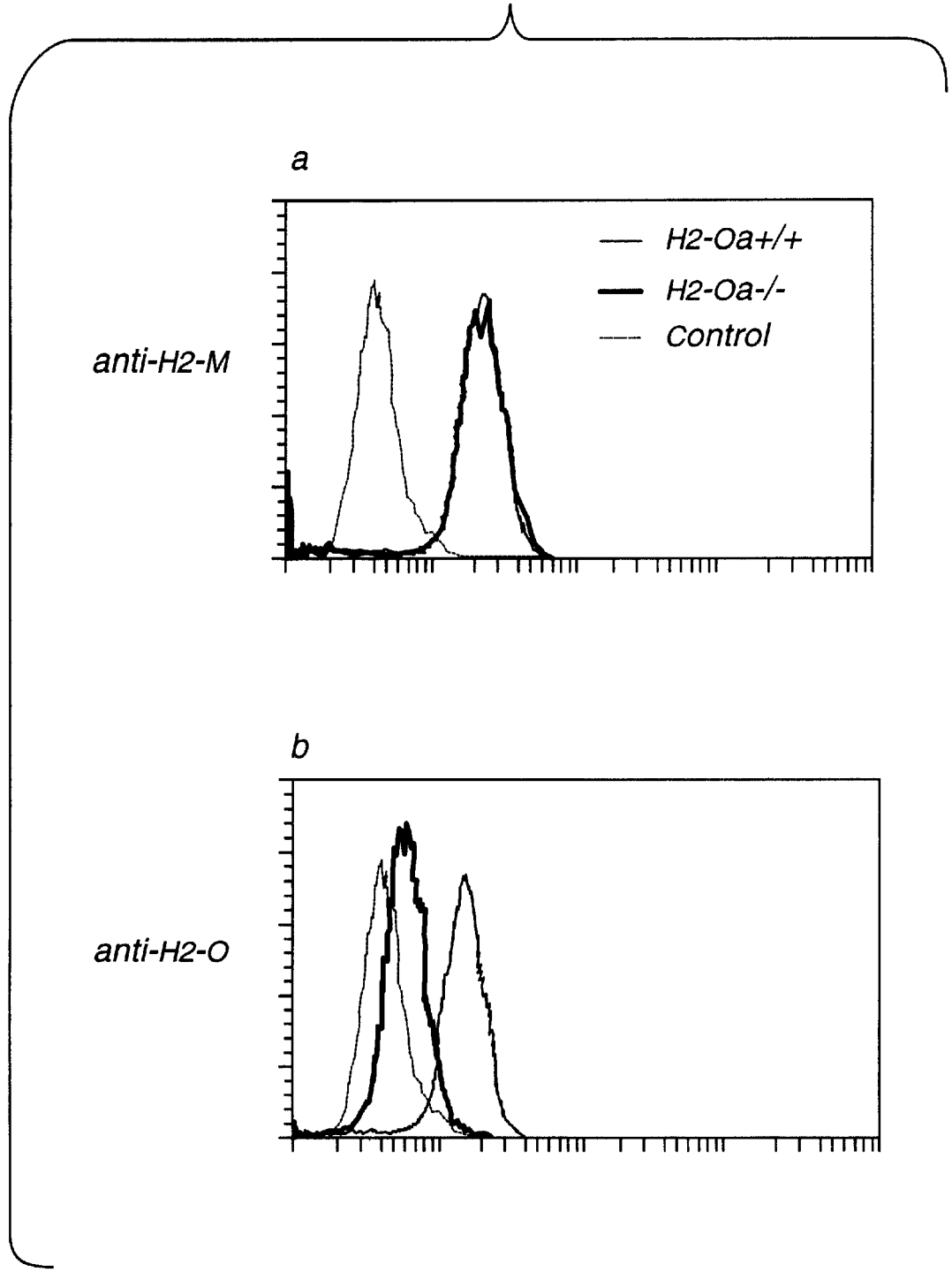

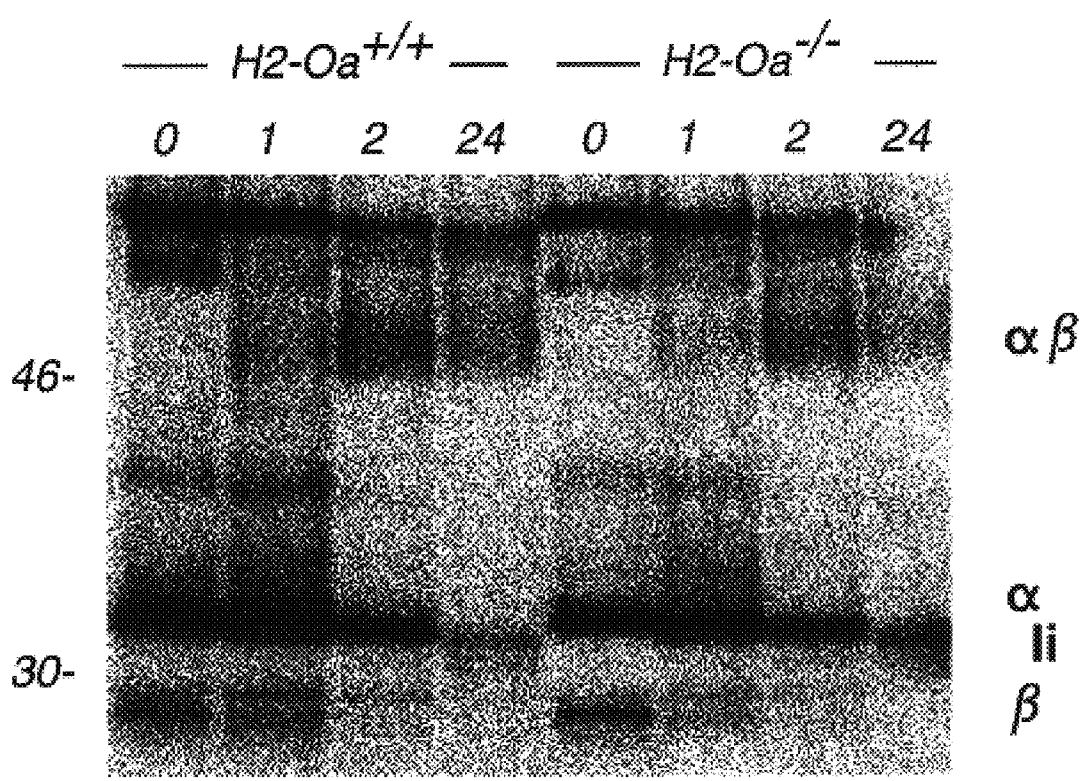

Binding of HA (306-318)

Release of Clip (81-104)

Release of HA (306-318)

METHODS FOR PRODUCING B CELLS AND ANTIBODIES FROM H2-O MODIFIED TRANSGENIC MICE

RELATED APPLICATIONS

This application is a continuation in part application of co-pending application Ser. No. 09/250,898, filed Feb. 16, 1999, abandoned, which is a non-provisional application of provisional application Ser. No. 06/074,847, filed Feb. 17, 1998, abandoned.

FIELD OF THE INVENTION

The present invention relates to transgenic nonhuman animals wherein an H2-O (the mouse equivalent of human HLA-DO), gene is altered, producing an animal lacking functional H2-O protein.

BACKGROUND OF THE INVENTION

Immediately after synthesis in the endoplasmic reticulum (ER), major histocompatibility complex (MHC) class II molecules associate with the invariant chain (Ii). Ii inhibits binding of peptides and nascent proteins to class II molecules in the ER and directs Ii-class II complexes to the endosomal system where binding of antigenic peptides occur (Wolf and Ploegh, 1995). Ii is degraded by proteolysis, but complete removal of class II-associated invariant chain peptides (CLIP) requires the catalytic function of HLA-DM (DM), a resident of the endosomal/lysosomal system which is structurally related to class II molecules (Fling et al., 1994; Karlsson et al., 1994; Morris et al., 1994; Sanderson et al., 1994). The absence of DM (or H2-M, the equivalent mouse molecule) leads to the accumulation of CLIP-containing class II molecules and decreased loading of antigenic peptides (Fung-Leung et al., 1996; Martin et al., 1996; Mellins et al., 1990; Miyazaki et al., 1996). In vitro, DM is sufficient to release CLIP peptides from class II molecules, but this effect is not restricted to CLIP (Kropshofer et al., 1997; Sloan et al., 1995; Weber et al., 1996). Thus, the dissociation rate of any peptide from class II molecules appears to be increased in the presence of DM, but remains proportional to the intrinsic dissociation rate of the peptide (Kropshofer et al., 1997; Weber et al., 1996). Whether DM-mediated release of peptides other than CLIP is important also in vivo is presently unknown. In B cells the majority of DM is associated with HLA-DO (DO) (Liljedahl et al., 1996), and a recent report has shown that association with DO inhibits the ability of DM to release CLIP, both in vitro and in transfected cells (Denzin et al., 1997). The physiological relevance of this effect is unclear however, since CLIP-containing class II molecules are not particularly prominent on B cells, the main, if not exclusive, cell type expressing DO (Douek and Altmann, 1997; Karlsson et al., 1991; Liljedahl et al., 1996; Tonelle et al., 1985; Wake and Flavell, 1985).

In contrast to dendritic cells, which are comitted to antigen presentation irrespective of antigen specificity (Cella et al., 1997), B cells are themselves antigen specific, but usually require T cell help in order to mature into antibody-secreting plasma cells (Vitetta et al., 1991). The antigens presented by B cells are mainly internalized by their immunoglobulin surface receptors (mIg) (Lanzavecchia, 1985; Rock et al., 1984) and receptor-independent antigen presentation by B cells, though well studied in vitro, is relatively inefficient. How B cells focus antigen presentation to antigens internalized by the B cell receptor is unclear, since increased antigen capture can only partly explain this phenomenon (Watts, 1997). It has been suggested that efficient B cell receptor-mediated antigen presentation may require specialized loading compartments (Mitchell et al., 1995; Watts, 1997) and several groups have described class II-rich intracellular compartments (Amigorena et al., 1994; Peters et al., 1991; Tulp et al., 1994; West et al., 1994). These compertments are not restricted to B cells, however (Calafat et al., 1994; Kleijmeer et al., 1994) and their functional importance is unclear. Though the general machinery for antigen processing is likely to be the same in different antigen presenting cells (APCs), it is still possible that cell-type specific differences in antigen processing may contribute to the efficient presentation of antigens internalized by mIg.

The present invention provides mice lacking H2-Oa to evaluate the importance of H2-O/DO for peptide loading and antigen presentation. Cells from H2-Oa-deficient mice were found to have normal levels of class II expression, and the density of H2-$A^b$-CLIP complexes at the cell surface was the same as in wild-type controls. However, B cells from H2-Oa deficient mice were found to have changed capacity to present protein antigens when compared to B cells from wild-type mice, showing that the absence of H2-O does modify the peptide content of class II molecules at the cell surface, either qualitatively or quantitatively. In older H2-Oa-deficient mice serum levels of immunoglobulin G1 (IgG1) were elevated, further showing that T-B cell interaction may be changed in these mice. Analysis of DO function in vitro, using recombinant molecules, confirmed the finding by Denzin et al. that DO inhibits DM function, but showed that the inhibition is decreased at acidic pH, suggesting that peptide loading may be favoured in acidic compartments (probably lysosomes) in the presence of DO.

SUMMARY OF THE INVENTION

To understand the functional role of H2-O in different cell types, mice that do not express the functional H2-O were generated by homologous recombination (HR) in embryonic stem (ES) cells and are disclosed herein. These mice provide a valuable animal model to understand the function of H2-O and to evaluate the therapeutic effects of drugs that modulate the function or the expression of H2-O equivalents in human cells.

Figure 1A:
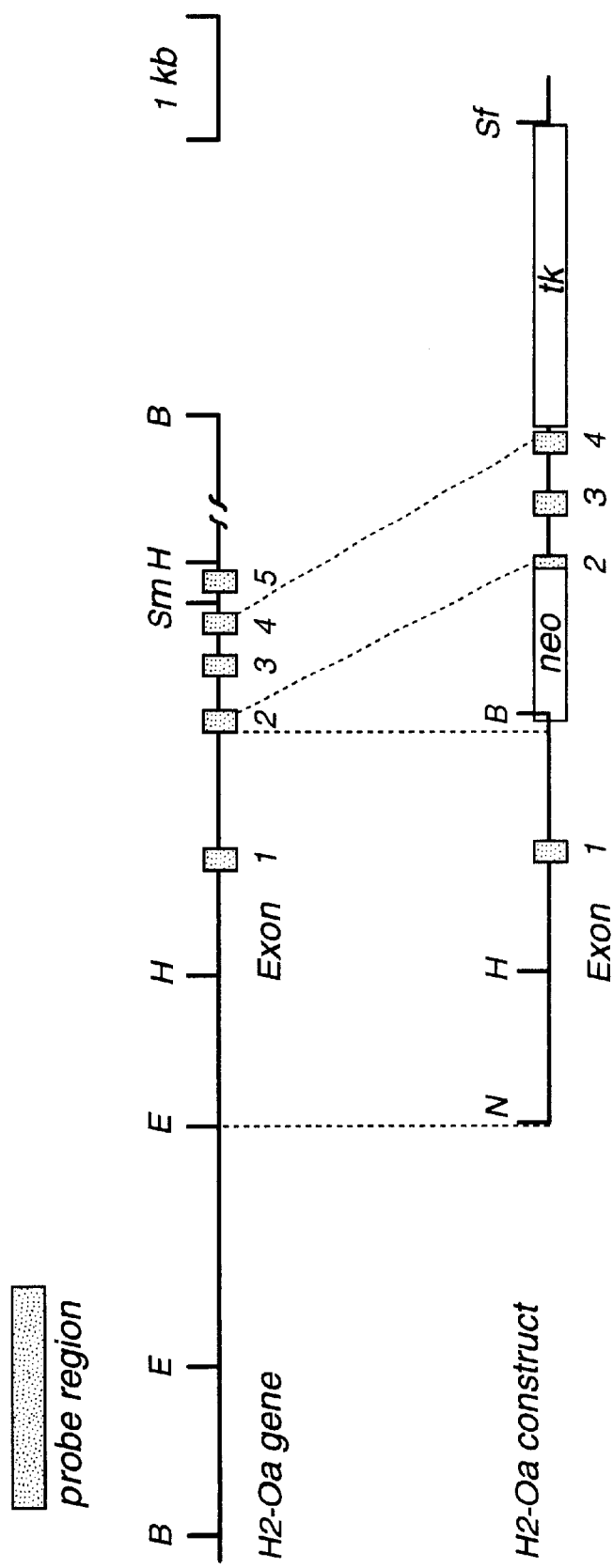
FIG. 1 Panels A–E show disruption of the mouse H2-Oa gene.

(A) The mouse H2-Oa gene and the knockout construct are shown. A neomycin resistant gene (neo) was inserted into exon 2 of the H2-Oa gene, and a herpes simplex-thymidine kinase gene (tk) was placed 3' end of the construct. Restriction sites are BamHI (B), EcoRI (E), HindIII (H), NotI (N), SfiI (Sf), SmaI (Sm). Numbered solid boxes are exons. A probe flanking 5' of the construct as shown were used in Southern hybridization to confirm homologous recombinations.

(B) Immunoprecipitation from $^{35}$S-labeled spleen cells. H2-$Oa^{+/+}$ (top) or H2-$Oa^{-/-}$ (bottom) splenocytes were labelled for 30 minutes (a, c) and either analysed immediately (0 min) or after chase in non-radioactive medium for 240 minutes (b, d). H2-Ob was immuno-precipitated from the cell lysates with rabbit antiserum K535 (anti-H2-Ob) and analysed by two-dimensional gel electrophoresis. Oap and Obp indicate non-transported forms of Oa and Ob. Acidic proteins are located to the right.

(C) Confocal images of H2-Oa$^{+/+}$ (a, b) or H2-Oa$^{-/-}$ (c, d) splenocytes stained with K535 (a, c) and 2E5A (anti-H2-M)(b, d).

(D) Analysis of H2-O and H2-M expression by flow cytometry. B cells from H2-Oa$^{+/+}$ (——) or H$_2$-Oa$^{-/-}$ () mice were permeabilized with saponin and stained with 2E5A for H2-M (a) or K535 for H2-Ob (b). The negative control staining (----) was the same in the two types of mice.

(E) Mouse tail genomic DNA was digested with restriction enzyme BamHI and hybridized with a 5' flanking probe. The probe was a ~300 basepair EcoRI-XhoI DNA fragment isolated from the probe region shown in FIG. 1A. The 12 kb DNA band of the endogenous H2-Oa gene that hybridized to the probe was changed to a 7 kb DNA band in the disrupted H2-Oa gene due to an insertion of a BamHI site in exon 2.

FIG. 2 Panels A–C show characterization of MHC class II expression in H2-Oa$^{-/-}$ mice and H2-O$^{+/+}$ littermates.

(A) Lymph node cells from wild-type (shaded), H2-Oa$^{-/-}$ () and H2-M$^{-/-}$ (----) mice were stained with antibodies reactive to H2-A$^b$(Y3P) or CLIP-containing H2-A$^b$(30-2 and 15G4) and analyzed by flow cytometry.

(B) Serial spleen sections from were stained for H2-O or H2-M with rabbit antisera K535 or K553, respectively. Locations of follicles (f), periarteriolar lymphocyte sheath (pals) and germinal centers (gc) are depicted.

(C) Immunoprecipitation from $^{35}$S-labeled spleen cells. H2-Oa$^{+/+}$ (left) or H2-Oa$^{-/-}$ (right) splenocytes were labelled for 30 minutes then either analysed immediately (0 min) or after chase in non-radioactive medium for the indicated time (in hours). H2-A$^b$ was immunoprecipitated and samples were analysed without prior boiling or reduction. Size markers are in kilodaltons.

FIG. 3 Panels A–C show antigen presentation by B cells and serum immunoglobulin levels.

(A) Presentation of antigens internalized by fluid phase to T cell hybridoma cells. Highly purified B cells from H2-O$^{+/+}$ (m) and H2-O$^{-/-}$ (s) mice were incubated with 0–800 μg/ml antigen (up to 400 μg/ml myoglobin) and T hybridoma cells overnight. IL-2 production by the hybridoma cells was measured in culture supernatants by ELISA.

(B) Presentation of antigens internalized by mIg receptor mediated uptake. B cells from transgenic H2-O$^{+/+}$ (m) and H2-O$^{-/-}$ (s) mice expressing anti-phosphorylcholine antibody were pulsed with phosphorylcholine conjugated antigens for 1 hour, then washed extensively to remove the excess antigen and incubated with hybridoma cells overnight. Values represent the mean IL-2 production ±SD from triplicate cultures. Levels of statistical significance between the means using students t-test are indicated (* P<0.05,  P<0.01, * P<0.005).

(C) Peptide presentation to HEL hybridoma cells. B cells from H2-O$^{+/+}$ (m) and H2-O$^{-/-}$ (s) mice were cultured overnight (18 h) with 0–1 μM hen egg lysozyme peptide (amino acids 74–91) in the presence of the HEL hybridoma. IL-2 production was measured as above.

Figure 4:
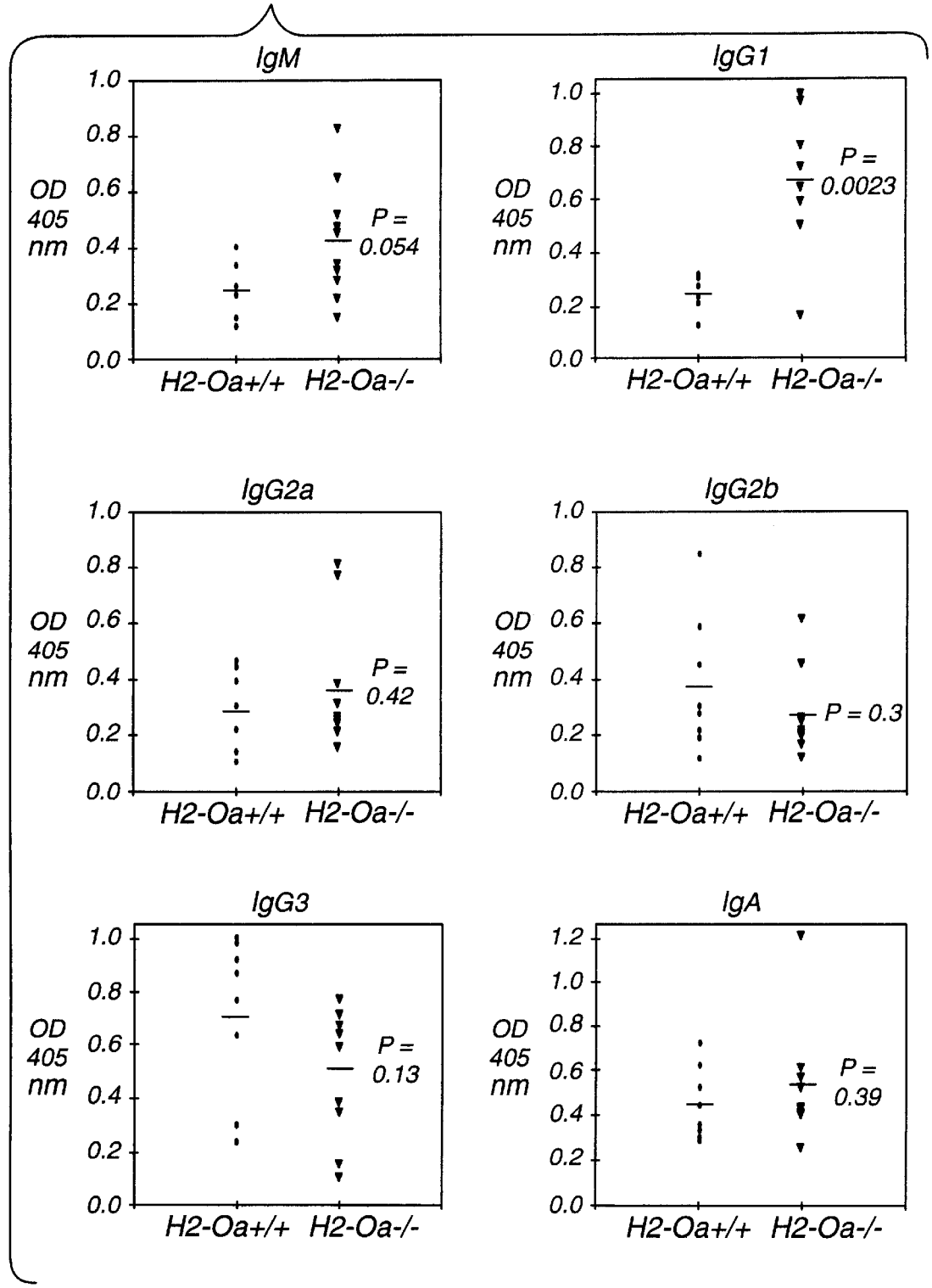

FIG. 4 shows immunoglobulin levels in sera. Sera from 10 months old sex-matched H2-O$^{+/+}$ (.) and H2-O$^{-/-}$ (t) mice were titrated and immunoglobulin levels were measured using isotype-specific ELISA. Bars represent mean serum levels expressed as OD at 405 nm.

Figure 5A:
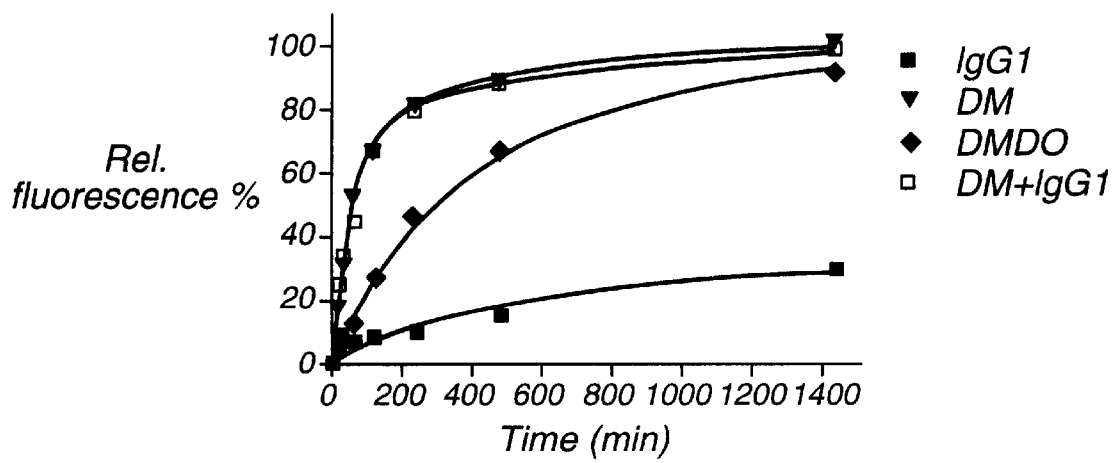
Figure 5B:
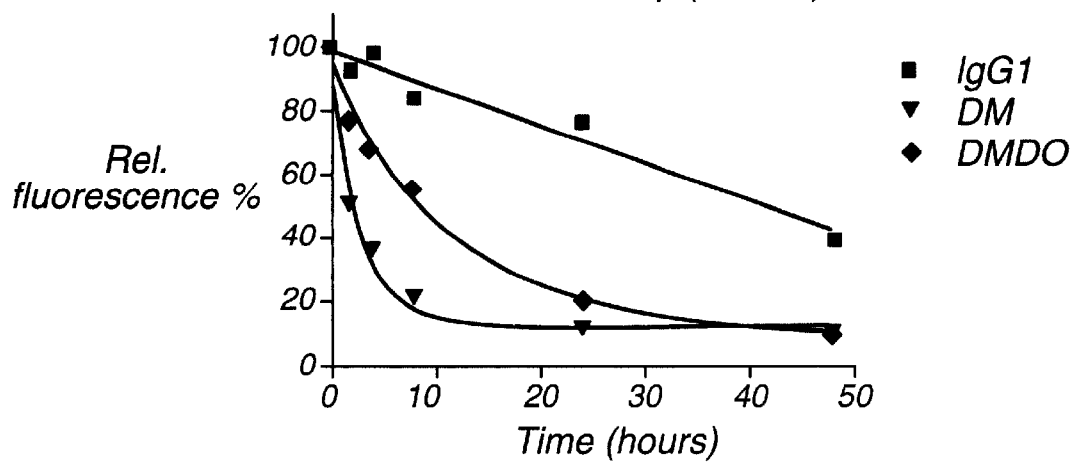
Figure 5C:
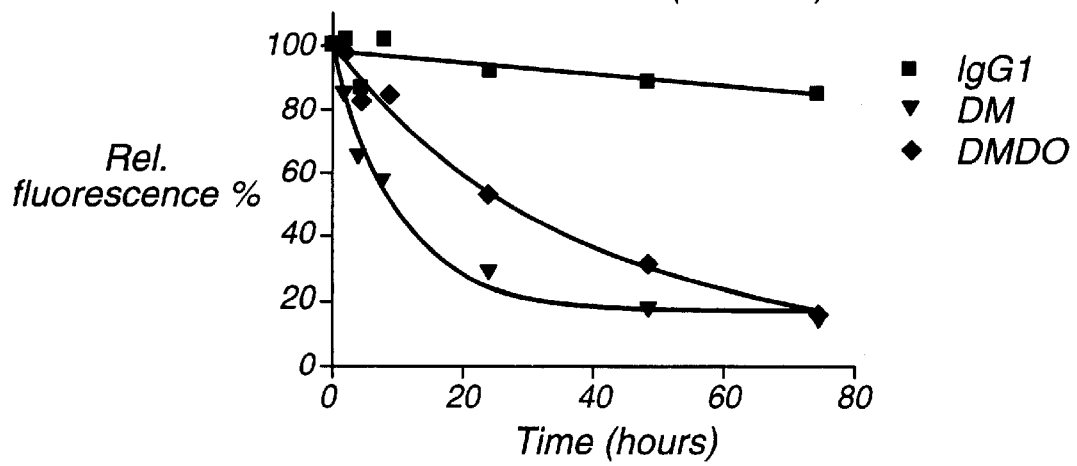

FIGS. 5A–5C show analysis of DO function in vitro (A) Kinetics of FITC-HA binding to DR1. DR1 (500 nM) was incubated with FITC-HA peptide (2.5 μM) alone or with the indicated proteins (DM 500 nM, DMDO 500 nM or DM 500 nM and IgG1 500 nM) for increasing lengths of time, as indicated at 37° C., pH 5.5. Samples were neutralized and free peptide was separated from DR-peptide complexes by gel filtration. 100% represents the binding in the presence of DM.

(B and C) Kinetics of FITC-CLIP (B) and FITC-HA (C) release from DR1. DR1 pre-loaded with FITC-labeled peptides was incubated with 5 μM unlabeled HA peptide alone or in the presence of DM (500 nM) or DMDO, (500 nM). Samples were treated as above. Fluorescence is given as % of the initial value.

Figure 6A:
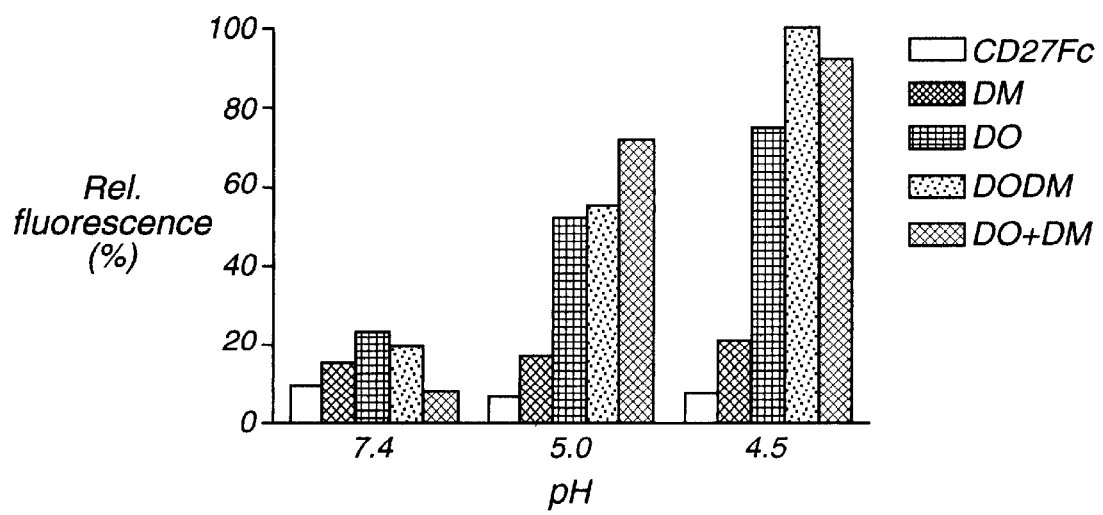

FIG. 6 Panels A–B show conformational changes in DO and DMDO upon acidification.

(A) Proteins (at 200 nM) were incubated at the indicated pH. ANS (1-anilinonaphtalene-8-sulphonic acid)(to 20 μM) was added and fluorescence was measured immediately.

(B) DM or DMDO (at 200 nM) were incubated at the indicated pH for 4 hours at 37° C. ANS (to 20 μM) was added and fluorescence was measured immediately. Samples were neutralised and re-measured immediately.

FIG. 7 Panels A–D show increased activity of DMDO at acidic pH.

(A) CD27Fc, DM or DMDO (125 nM) were incubated at 37° C. for 3 hours at the indicated pH before addition of DR1 (250 nM) and FITC-HA peptide (5 μM). Samples were incubated for 1.5 hours at 37° C., then neutralized and analyzed as in FIG. 5. 100% represents the binding in the presence of DM at pH 5.5.

(B) Kinetics of FITC-HA binding to DR1 (500 nM) in the presence of CD27, DMDO, papain-digested DMDO, or in-vitro-formed DMDO complexes (DMDO Mix), all at 500 nM. Samples were incubated for increasing lengths of time, as indicated at 37° C., pH 5.5 or at pH 4.5, then analyzed as in FIG. 5. 100% indicates the maximal fluorescence in the presence of DMDO at pH 4.5.

(C, D) Kinetics of FITC-HA binding to DR1 (500 nM) in the presence of CD27 (500 nM), DMDO (500 nM) and two dilutions of DM (64 nM and 20 nM) at pH 5.5 (C) or pH 4.5 (D). Samples were incubated at and analysed as above. 100% indicates the maximal fluorescence in the presence of DMDO at pH 4.5.

Figure 8:
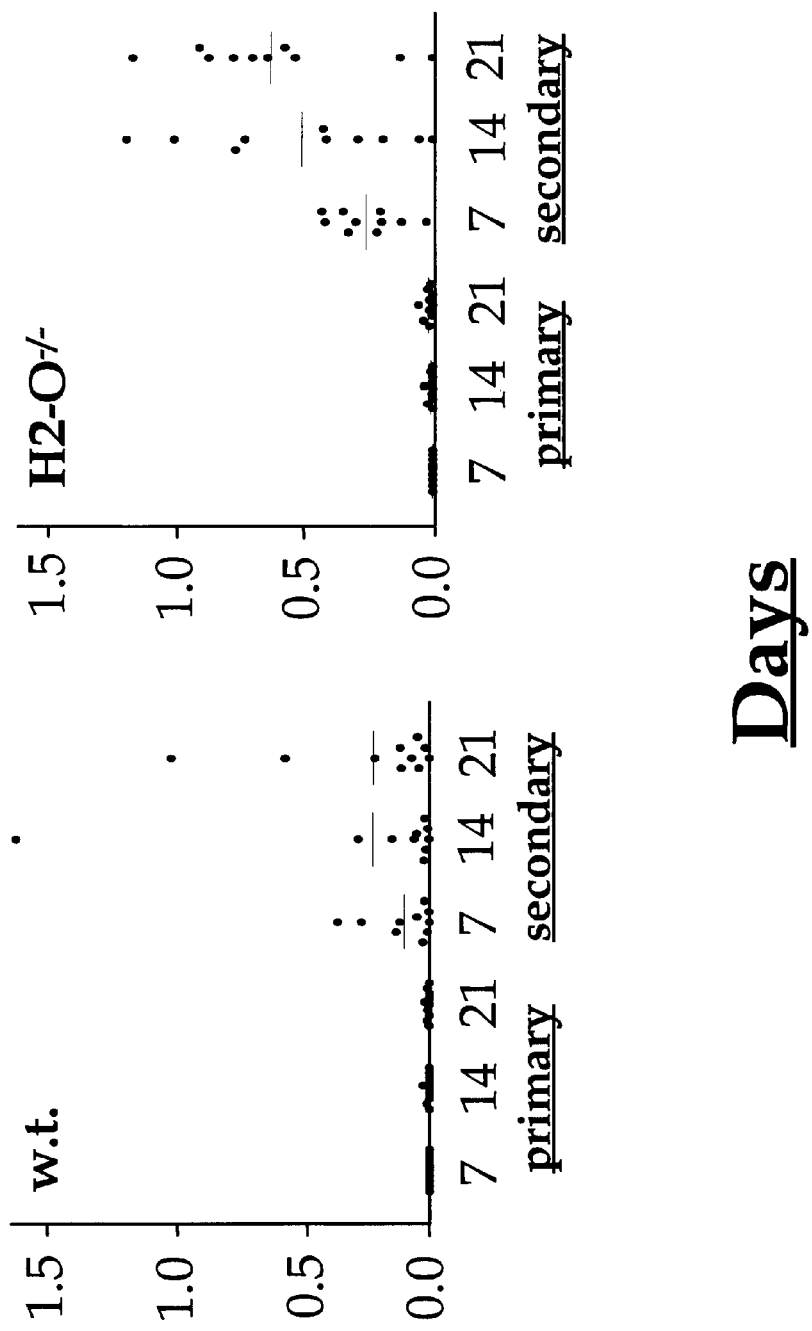

FIG. 8 shows the ratio of high affinity IgG1 (measured by the binding to NP-BSA-2.5) to the total amount of antigen-specific IgGl (measured by the binding to NP-BSA-23) after low dose immunization with NP-OVA.

Figure 9:
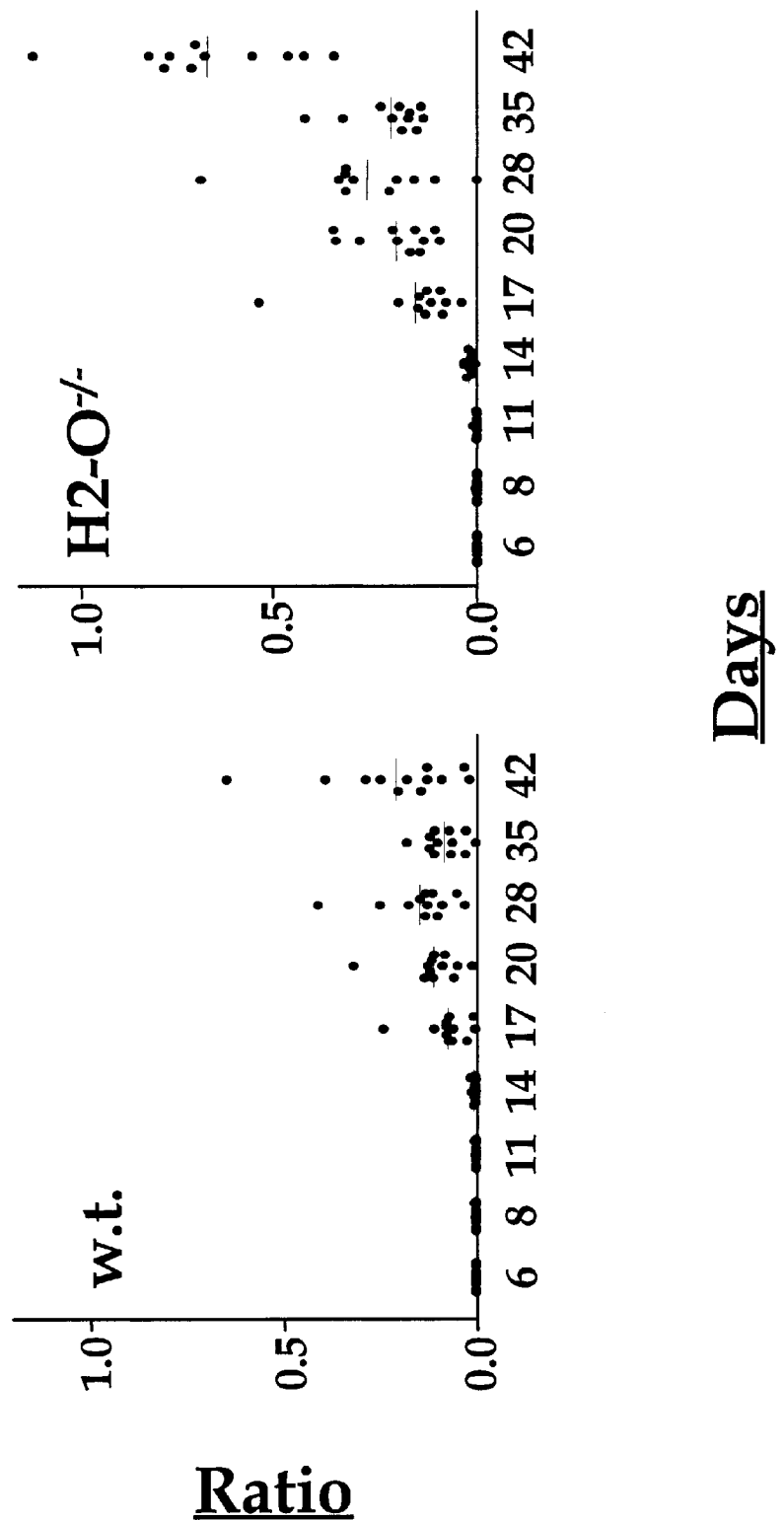

FIG. 9 shows the ratio of high affinity IgGl (measured by the binding to NP-BSA-2.5) to the total amount of antigen-specific IgGl (measured by the binding to NP-BSA-23) with high dose immunization with NP-OVA.

DETAILED DESCRIPTION OF THE INVENTION

The H2-O knockout mice that were generated in the present invention provide a model in which the H2-Oa gene was disrupted by homologous recombination (HR). The process of generating the knockout mice can be divided into 4 basic stages:

1. cloning of the H2-O gene and preparation of DNA construct for transfection of embryonic stem (ES) cells;
2. isolating ES cells in which the H2-Oa gene has been disrupted by HR;

3. generating chimeric mice from mouse embryos injected with the knockout ES cells; and 4. breeding chimeric mice to obtain knockout mice through germline transmission.

The present invention utilizes a cloned genomic DNA encoding the H2-O protein and describes the cloning and characterization of the mouse H2-Oa gene. Transgenic animals are generated which have altered the H2-Oa gene. The alterations to the naturally occurring gene can be modifications, deletions and substitutions. Modifications and deletions render the naturally occurring gene nonfunctional, producing a "knockout" animal. Substitution of the naturally occurring gene for a gene from a second species results in an animal which produces the gene product of the second species. Substitution of the naturally occurring gene for a gene having a mutation results in an animal which produces the mutated gene product. These transgenic animals are critical for drug antagonist or agonist studies, the creation of animal models of human diseases, and for eventual treatment of disorders or diseases associated with HLA-DO-mediated responses. A transgenic animal carrying a "knockout" of H2-O is useful for the establishment of a nonhuman model for diseases involving H2-O equivalents in the human.

A transgenic mouse carrying the disrupted H2-Oa gene was generated by homologous recombination of a target DNA construct with the endogenous gene in the chromosome. The DNA construct was prepared from a genomic clone of H2-Oa which was isolated from a genomic DNA library.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at a subcellular level, such as by targeted recombination or microinjection or infection with recombinant virus. The term "transgenic animal" is not intended to encompass classical cross-breeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact possess some or all of that alteration or genetic information, they are transgenic animals as well.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene, or not expressed at all.

The altered H2-Oa gene generally should not fully encode the same H2-O as native to the host animal, and its expression product should be altered to a minor or great degree, or absent altogether. However, it is conceivable that a more modestly modified H2-O gene will fall within the scope of the present invention.

The genes used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro [M. J. Evans et al., Nature 292: 154–156 (1981); M. O. Bradley et al., Nature 309: 255–258 (1984); Gossler et al. Proc. Natl. Acad. Sci. USA 83: 9065–9069 (1986); Robertson et al., Nature 322, 445–448 (1986); S. A. Wood et al. Proc. Natl. Acad. Sci. USA 90: 4582–4584 (1993)]. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal (R. Jaenisch, Science 240: 1468–1474 (1988)).

Since H2-O is an independent component of a complex mechanism, the proteins, including that encoded by H2-Oa DNA, must be examined both individually and as a group if their contribution to the mechanisms are to be understood. One approach to the problem of determining the contributions of individual genes and their expression products is to use isolated genes to selectively inactivate the native wild-type gene in totipotent ES cells (such as those described herein) and then generate transgenic mice. The use of gene-targeted ES cells in the generation of gene-targeted transgenic mice was described in 1987 (Thomas et al., Cell 51:503–512, (1987)) and is reviewed elsewhere (Frohman et al., Cell 56:145–147 (1989); Capecchi, Trends in Genet. 5:70–76 (1989); Baribault et al., Mol. Biol. Med. 6:481–492, (1989); Wagner, EMBO J. 9: 3025–3032 (1990); Bradley et al., Bio/Technology 10: 534–539 (1992)).

Techniques are available to inactivate or alter any genetic region to any mutation desired by using targeted homologous recombination to insert specific changes into chromosomal genes. Homologous recombination was reported to be detected at frequencies between $10^{-6}$ and $10^{-3}$ (Lin et al., Proc. Natl. Acad. Sci. USA 82:1391–1395 (1985); Smithies et al., Nature 317: 230–234 (1985); Thomas et al., Cell 44:419–428, (1986); Song et al., Proc. Natl. Acad. Sci. USA 84:6820–6824 (1987)). Nonhomologous plasmid-chromosome interactions are more frequent, occurring at levels $10^5$-fold (Lin et al., Proc. Natl. Acad. Sci. USA 82:1391–1395 (1985)) to $10^2$-fold (Thomas et al., Cell 44:419–428 (1986); Song et al., Proc. Natl. Acad. Sci. USA 84:6820–6824 (1987)) greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening individual clones (Kim et al., Nucleic Acids Res. 16:8887–8903 (1988); Kim et al., Gene 103:227–233 (1991)). Alternatively, a positive genetic selection approach has been developed in which a marker gene is constructed which will only be active if homologous insertion occurs, allowing these recombinants to be selected directly (Sedivy et al., Proc. Natl. Acad. Sci. USA 86:227–231 (1989)). One of the most powerful approaches developed for selecting homologous recombinants is the positive-negative selection (PNS) method developed for genes (such as H2-Oa) for which no direct selection of the alteration exists (Mansour et al., Nature 336:348–352: (1988); Capecchi, Science 244:1288–1292, (1989); Capecchi, Trends in Genet. 5:70–76 (1989)). The PNS method is more efficient for targeting genes which are not expressed at high levels because the marker gene has its own promoter. Nonhomologous recombinants are selected against by using the Herpes Simplex virus thymidine kinase (HSV-TK) gene flanking the DNA construct. Cells with nonhomologous insertion of the construct express HSV thymidine kinase and therefore are sensitive to the herpes drugs such as gancyclovir (GANC) or FIAU (1-(2-deoxy 2-fluoro-B-D-arabinofluranosyl)-5-iodouracil). By this counter-selection, the number of homologous recombinants in the surviving transformants can be increased.

As used herein, a "targeted gene" or "knockout" is a DNA sequence introduced into the germline of a non-human animal by way of human intervention, including but not limited to, the methods described herein. The targeted genes of the invention include DNA sequences which are designed to specifically alter cognate endogenouos genes.

All the above applications have to be verified in animal tests and eventually clinical trials. One approach to determine the functional role of the drug target is to study the defects resulting from the disrupted gene in a whole animal. The H2-O knockout mice that have been generated and are disclosed herein will allow the definition of the function of H2-O which is critical in deciding the types of modulators are most suitable in therapies.

Any H2-O function that is detected in the knockout mice of the present invention would provide evidence of the existence of alternative novel H2-O subtypes which may then be isolated from the knockout mice of the present invention.

The absence of functional H2-O in the knockout mice of the present invention are confirmed in RNA analysis, protein expression detection, receptor binding assays and other receptor functional studies. For RNA analysis, RNA samples are prepared from different organs of the knockout mice and the H2-O transcript are detected in Northern blots using oligonucleotide probes specific for the transcript.

Polyserum and monoclonal antibodies that are specific for the mouse H2-O are produced. The absence of intact H2-O in the knockout mice are studied in flow cytometric analysis, in immunohistochemical staining, and in receptor binding assays using H2-O-specific antibodies. Alternatively, functional assays are performed using preparations of different cell types collected from the knockout mice.

In this study we have used H2-Oa-deficient mice to address the functional relevance of H2-O for antigen processing and presentation. We find that H2-O influences the loading of peptides to class II molecules (i.e. H2-$A^b$) in B cells, since protein antigens were presented differently to antigen-specific T cell hybridomas depending on whether the presenting B cells expressed H2-Oa or not. When the analyzed antigens were internalized by fluid phase endocytosis all were presented better (to varying degrees) by B cells from H2-Oa-deficient mice than by B cells from wild-type mice. In contrast, the same antigens were either presented better or equally well by B cells from wild-type mice when internalized by a transgenic mIg receptor, suggesting that the presence of H2-O results in discrimination between different forms of antigen uptake.

The H2-$A^b$ in H2-Oa-deficient mice appear to contain a mixture of peptides and have essentially normal reactivity with anti-H2-$A^b$ antibodies. Furthermore, the cell surface expression of CLIP-H2-$A^b$ was found to be essentially identical on both resting and activated B cells from wild-type or H2-Oa-deficient mice. This finding was somewhat unexpected, considering that Denzin et al. have convincingly shown that expression of DO inhibits DM-mediated CLIP release in transfected cell lines, resulting in increased surface levels of CLIP-class II complexes (Denzin et al., 1997).

It is not clear why expression of an additional molecule inhibiting DM function would be more favorable than controlling the transcription of DM itself, unless DO either changes the specificity of DM, or provides a mechanism for more rapid shifts in DM activity than can be achieved by transcriptional regulation. Cellular activation or signal transduction events could potentially result in the dissociation of DMDO complexes, thus releasing free DM. However, crosslinking of mIg on B cell lines or splenocytes, as well as antigen-non-specific stimulation with lipopolysaccharide (LPS) or phorbol esters, do not result in readily detectable dissociation or post-translational modifications of DMDO (or H2-M-H2-O) complexes. There is presently no evidence to suggest that DM activity would be controlled by intracellular signalling events.

The specificity of peptide loading could be changed either directly or indirectly by the presence of DO/H2-O. A possible direct effect was analyzed using purified recombinant molecules, and in this system we were able to confirm the previously published data (Denzin et al., 1997) (obtained with detergent solubilized material from B cell lines) showing that DMDO complexes were distinctly less active than DM alone in mediating CLIP release. However, other peptides than CLIP appeared to be released from class II molecules with slower kinetics by DMDO than by DM, suggesting that DO did not directly change the specificity of DM-mediated peptide release.

An alternative explanation, supported by our biochemical data, suggest that DO indirectly influences the specificity of DM-mediated peptide release by limiting the pH interval where DM is fully active. Thus, while DM was active in a relatively broad pH range between pH 6.0 and 4.5, the DMDO complexes had low activity above pH 5.5. At lower pH, however, the DMDO complexes were almost as active as DM alone, suggesting that association with DO decreases the pH optimum for DM-mediated peptide exchange, or rather that association with DO narrows the pH range where DM is active. It is not clear whether DMDO complexes dissociate at acidic pH to release free active DM, or whether the complexes interact directly with DR molecules. We have not been able to detect DR-DMDO complexes, but it can not presently be excluded that they exist. It should be pointed out that some free DM will undoubtedly exist in the endocytic pathway also if DO is expressed, since the two molecules are non-covalently associated.

The pH-dependent differences in activity between DM and DMDO complexes suggest that the differences in antigen presentation observed between the H2-O-deficient and the wild-type mice may reflect a skewing of the localization for peptide loading to more acidic compartments in the presence of H2-O. This could potentially result either in decreased or increased presentation of a certain epitope depending where it becomes accessible as well as how sensitive it is to destruction. The competition by other peptides for binding to class II molecules will also influence the probability of presenting particular epitopes. In addition, different class II molecules have varying pH requirements for peptide loading and this factor is also likely to influence how they are affected by the presence or absence of H2-O. Preferred peptide loading in lysosomes could be advantageous in the case of B cells where relevant antigens are internalized by mIg (Lanzavecchia, 1985; Rock et al., 1984). Protein domains are often stabilized by their interaction with antibodies (Accolla et al., 1981; Jemmerson and Paterson, 1986; Simitsek et al., 1995) and high affinity antigen-antibody complexes may require lysosomal conditions for the release of antigenic epitopes, due to the protease resistance of the antibody itself. Decreased H2-M activity in endosomal compartments (due to the association with H2-O) would limit the risk of presenting antigens internalized by fluid phase or low affinity receptors, without seriously limiting the presentation of antigens internalized by high affinity mIg. The elevated IgG1 titers in the H2-O deficient mice may reflect increased activation of B cells in response to antigens taken up by fluid phase or low affinity receptors. During an immune response, activation of $CD4^+$ T cells by B cells presenting peptides from such antigens could potentially result in the expansion of T and B cells with irrelevant or harmful specificities. This could result in the dilution of an effective immune response, but also to the expansion of autoreactive cells, thus increasing the risk for autoimmune reactions. The presence of H2-O/DO in B cells may thus serve to focus antigen presentation to antigens internalized by mIg in order to increase the specificity of the immune response and to avoid reactivity to self antigens.

The following Examples are presented for the purpose of illustrating the present invention and are not to be construed as a limitation on the scope of this invention.

EXAMPLE 1

Gene Targeting

A 4.3 kb DNA fragment from a 129/Ola mouse genomic clone covering most of the H2-Oa gene was used in the knockout construct. A cassette containing a neomycin resistance gene was inserted into exon 2. An HSV-thymidine kinase cassette was placed at the 3' end of the construct. The DNA construct was introduced into E14 embryonic stem cells by electroporation. Cells were cultured in the presence of 400 µg/ml G418 and 0.2 µM ganciclovir. ES cells with the targeted gene were detected by polymerase chain reaction and then confirmed by Southern hybridization using DNA probes flanking the construct.

$H2-Oa^{-/-}$ or $H2-Oa^{+/+}$ mice were bred with transgenic 207-4 mice (Storb et al., 1986) (on C57BL/6 background). Expression of the transgene was tested with ELISA against pc-conjugated protein.

Transfection of ES Cells with the H2-O DNA Constructs

The final DNA construct was linearized by complete digestion with restriction enzymes Not I, or SfI, or both. DNA was then precipitated by 2 volumes of ice cold ethanol at −20° C. for 1 hour. Precipitated DNA was pelletized by centrifugation, rinsed once with 0.5 ml 70% ethanol, air dried and then dissolved at 1 mg/ml in phosphate-buffered saline (Gibco).

Embryonic stem (ES) cells E14 (Hooper et al., 1987, HPRT-deficient (Lesch-Nyhan) mouse embryos derived from germline colonization by cultured cells. Nature 326, 292–295) were maintained at an undifferentiated stage by co-culturing with embryonic fibroblasts (EF) and in culture medium DMEM (15% FCS, 1 mM sodium pyruvate, 0.1 mM b-mercaptoethanol, 2 mM L-glutamine, 100 U penicillin and 100 U streptomycin) containing 1000 U/ml leukemia inhibitory factor (LIF) (Gibco). EF cells were primary fibroblast cultures prepared from day 15–17 mouse fetuses according to the method described by Robertson (Robertson, E. J. (1987) Embryo-derived Stem Cell Lines. In: Teratocarcinomas and Embryonic Stem Cells. E. J. Robertson, ed. (Oxford, Washington DC: IRL Press), p 71–112.). EF were treated with 10 mg/ml mitomycin C (Sigma) in culture medium for 2 hours to stop cell division prior to the use as feeder cells. For DNA transfection, ES cells were harvested by trypsin treatment and resuspended at $6.25 \times 10^6$ cell/ml in culture medium. DNA construct (20 µg) was added to 0.8 ml of ES cell suspension for electroporation at 250 µF and 340 Volts using the Gene Pulser (BioRad).

Transfected ES cells were plated onto EF coated 90 mm plates at $2.5 \times 10^6$/plate in culture medium. Two days later, cells were subjected to drug selection in medium containing 400 µg/ml G418 (Geneticin, Gibco) and 2 µM GANC (Cytosin, Syntex). Culture medium was changed daily. Massive cell death was obvious starting day 4 and most of the dead cells were removed through daily medium change. Surviving cell colonies were observable under microscope by day 7 and by day 10 they were visible on the plates without a microscope.

PCR Screen of Transfected ES Cells for Homologous Recombination

The size of ES colonies on day 11 after transfection was large enough for PCR screening. To collect cell colonies, culture medium in the 90 mm plates was aspirated and 10 ml PBS was added. Individual cell colonies were located with the aid of a stereomicroscope, collected in a 20 µl volume with an autopipetteman and transferred into 96 well-plates. To prepare single cell suspension of the ES colonies, 25 µl of 0.25% trypsin (Gibco) was added per well in 96 well-plates. After 8 minutes of trypsin treatment at 37° C., 25 µl of culture medium was added. All the ES colonies were still maintained in culture as master plates while screening by PCR for homologous recombination events was performed. To prepare master plates, 60 µl of each cell sample was transferred to 96-well plates which had been coated with EF cells and contained 180 µl/well of the culture medium containing G418 and GANC.

For the first round PCR screen, each cell lysate sample was prepared from 12 cell colonies which arrayed as one row of samples in the 96 well-plates. After the preparation of master plates, the remaining cell samples of about 90 µl/well on every row of the plates were pooled. Cells were pelleted in tubes by centrifugation for 1 minute. After draining all the medium, cells were lysed by adding 30 µl distilled water and brief vortexing. Cell lysates were prepared by first heating at 95° C. for 10 minutes, cooling to room temperature and followed by an addition of 1 ml proteinase K (10 mg/ml in water) with brief vortexing, a 90 minute incubation at 50° C. for proteinase K digestion, and then 10 minutes at 95° C. for heat inactivation of proteinase K.

PCR was carried out using the 9600 GeneAmp system (Perkin Elmer). The reaction mixtures contained 5 µl cell lysate, 4 µM of each of the two oligonucleotide primers, 200 µM each of dATP, dTTP, dCTP, and dGTP, and 5 U AmpliTaq DNA polymerase in PCR buffer (10 mM Tris-Cl, pH8.3, 50 mM KCl, 1.5 mM $MgCl_2$ and 0.001% w/v gelatin). The reaction condition was 3 cycles of 2 min at 94° C., 2 min at 60° C., and 2 min at 72° C., then 40 cycles of 15 sec at 94° C., 15 sec at 60° C., and min at 72° C., followed by 7 min at 72° C. PCR primers that were used to amplify homologous recombination were: Oa-INT4R(5'-CCTCCCTTTGCCCACAGACTCCCG-3')[SEQ.ID.NO.:1] and neo-1488 (5'-GATTCGCAGCGCATCGCCTTCTAT-3') [SEQ.ID.NO.:2] and the size of the amplified DNA is expected to be about 1 Kb.

To detect the specific DNA fragment amplified by PCR, 20 µl of the PCR samples were separated according to size by 1% agarose gel electrophoresis, blotted onto Hybond-N+ nylon membranes (Amersham), and hybridized to the $P^{32}$-labelled oligonucleotide probe Oa-839R (5'-GTGATCATGAGCACGGTGCCCAGGAGGCAGCCC-3') [SEQ.ID.NO.:3] which is located within the amplified DNA fragment. PCR samples with a 1 Kb DNA band detected by the oligo probe were considered as putative positive groups for further screening.

ES cells in master plates after 3–4 days culture were ready for splitting. Cell colonies in the positive groups were screened individually by a second round of PCR to identify the positive individual colonies. To maintain the positive groups in culture, cells in the wells were trypsinized by first removing the culture medium, rinsing once with 50 μl PBS, treating with 40 μl 0.25% trypsin for 5 minutes at 37° C., followed by adding 90 μl culture medium. Cells were then resuspended and 20 μl of the cell samples were transferred to master plates which had been coated with EF and filled with 200 μl culture medium containing G418 and GANC. The remaining cells (110 μl/well) were transferred into eppendorf tubes. Cell lysates were prepared and homologous recombination signals were amplified by PCR and detected by hybridization as described in the previous paragraphs.

Confirmation of Homologous Recombination by Genomic Southern Hybridization

ES cells derived from the positive colonies in PCR screen were expanded in culture and DNA was extracted as described by Maniatis et al. (Maniatis, T.; Fritsch, E. F.; Sambrook, J. (1982) Molecular Cloning, Cold Spring Harbor Laboratory pp. 280–281). Genomic DNA samples of the putative knockout cell lines were digested with the restriction enzymes BamHI, separated by 1% agarose gel electrophoresis, blotted onto Hybond-N+ nylon membranes (Amersham) and hybridized with a 300 bp EcoRI-XhoI DNA fragment within the EcoRI-EcoRI region as shown in FIG. 1A. This DNA probe did not hybridize to the DNA constructs that were integrated randomly in the chromosome. The normal H2-Oa gene in chromosomal DNA was detected as a DNA band>12 Kb and the disrupted gene as a 5.7 Kb DNA band resulting from an introduced BamHI site 5' to the neomycin resistance gene (FIG. 1A).

Generation of Chimeric Mice by Embryo Injection

Mouse embryos at 3.5 day gestation stage were collected from the uteri of superovulated C57BL/6J mice. About 10–15 ES cells were injected into the blastocoel cavity of the embryos. Injected embryos were transferred into the uteri of pseudopregnant CD1 mice at 2.5 day gestation. Mice developed from these embryos were born 17 days later. Since the ES cells used were derived from the 129 Ola mouse strain with the dominant agouti coat color genes, chimeric mice were identified by the agouti coat color from ES derived cells, versus the black color from C57BL/6J embryos.

ES Germline Mice Obtained by Chimeric Mouse Breeding

Chimeric mice were bred with C57BL/6J mice. These crosses are performed to test for the germline transmission of ES cells. Some of the progeny from the breeding are expected to be agouti if the chimeric male had germ line cells derived from ES cells which carry the dominant agouti coat color genes.

Figure 1B:
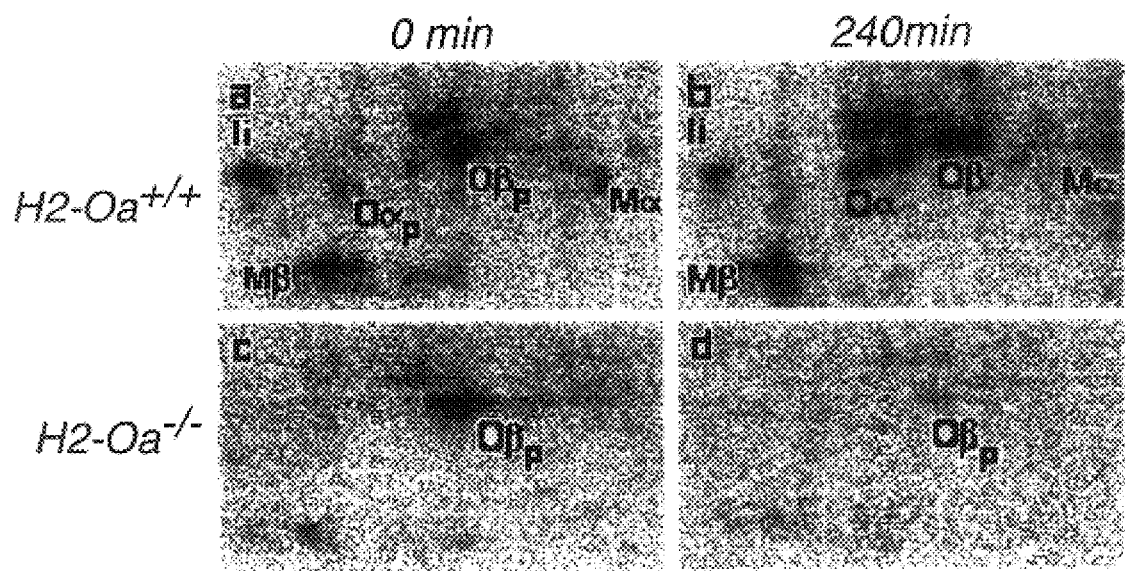
Figure 1C:
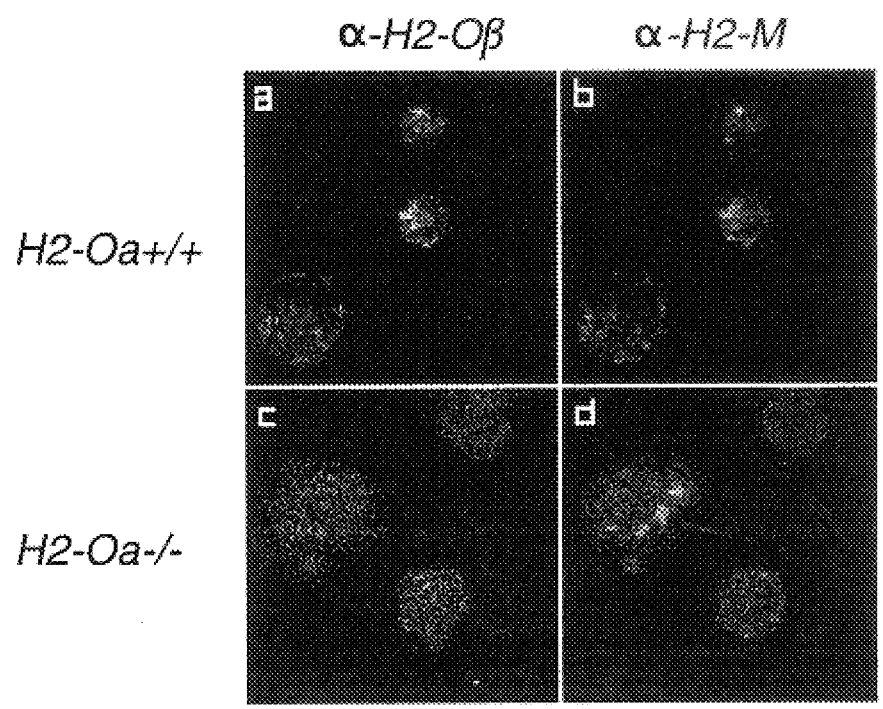
Figure 1E:
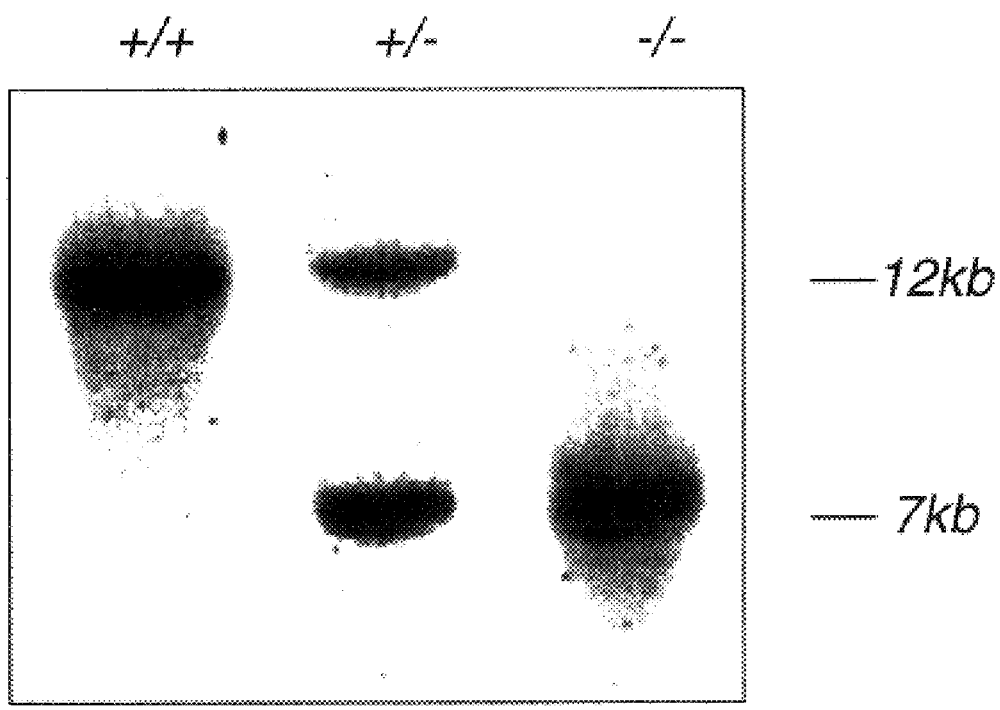

Germline mice that were heterozygous for the disrupted H2-O gene were identified by analysis of tail DNA in Southern hybridization as described in the previous paragraph. To determine the H2-O genotypes, genomic DNA is purified from about 1 cm of tail from each agouti mouse after weaning. The genomic DNA is isolated as described (Laird et al., supra), followed by phenol and phenol:chloroform extractions and ethanol precipitation. Genomic DNAs are digested with BamHI, and hybridized with the 5' flanking DNA probe (shown in FIG. 1A). Southern hybridization analysis confirms that the structure of the altered H2-Oa gene is identical to that predicted, and previously characterized in the H2-O targeted ES clones (FIG. 1E).

Generation of Homozygous Knockout Mice from Breeding of Heterozygous Knockout Mice Male and female heterozygous knockout mice, each of which contained one copy of the altered H2-O gene, were mated with each other to generate mice in which both copies of the H2-O gene are disrupted. It was predicted that one fourth of the mouse embryos would be homozygous for the altered H2-O gene. Surviving offspring were genotyped by Southern hybridization as described above. Homozygous mutant mice are born at a ratio of 1 in 4 pups if the defective gene does not affect embryo development. Homozygous mutant mice were identified by analysis of tail DNA samples. DNA patterns of knockout mice are shown in FIG. 1E.

EXAMPLE 2

Characterization of H2-O Knockout Mice
Class II Expression in H2-Oa-deficient Mice
Flow Cytometry and Immunofluorescence Cells were attached to coverslips coated with Cell-Tak (Collaborative Biomedical Research, Bedford, MA) before fixation with 4% formaldehyde-PBS. After fixation cells were washed with 50 mM $NH_4Cl$, PBS. Antibody incubations were made in PBS with 0.6% fish skin gelatin and 0.2% saponin for permeabilization. FITC labeled anti-rabbit Ig (Cappel) and Texas-Red labeled anti-mouse or anti-rat Ig (Molecular Probes) secondary reagents were used. Fluorescent cells were imaged using a Bio-Rad confocal microscope.

Lymph node and spleen cells were stained with biotinylated anti-IgM (μ-specific) (Jackson ImmunoResearch), M5/114, Y3-P, 30-2, BP107, KH74, B220 or J11d followed by FITC-streptavidin (Jackson ImmunoResearch). For 15G4 (mouse IgG1) anti-IgG (Fcg-specific F(ab')$_2$) was used for secondary staining. Cells were also double stained with biotinylated anti-CD5, CD16, CD19, CD22, CD23, or IgD followed by FITC-streptavidin and PE-conjugated anti-B220. Cells from lymph node and thymuses were double stained with FITC-conjugated anti-CD8 and PE-labeled anti-CD4 as previously described (Surh et al., 1992). For staining of permeabilized cells, B cells were stained in 1% FCS with 0.1% azide and 0.02% saponin without fixation using biotinylated K535 (anti-H2-Ob) or 2E5A (anti-H2-M) (Fung-Leung et al., 1996) followed by FITC-streptavidin.

Figure 2A:
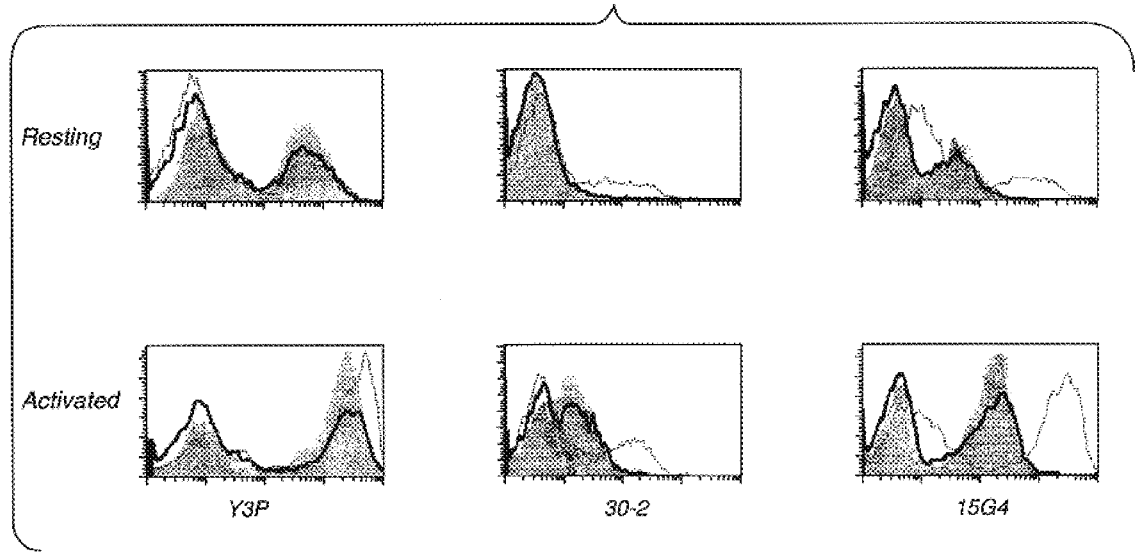

In mice lacking H2-M, the cell surface levels of H2-$A^b$ are normal, but the peptide content of these molecules is changed, so that the vast majority of molecules contain CLIP. The class II expression at the cell surface of lymph node cells from H2-Oa-deficient mice was analyzed by flow cytometry. As controls, cells from wild-type and H2-M-deficient mice were analyzed. The density of H2-$A^b$ expression on H2-Oa$^{-/-}$ lymph node cells (which contain both B and T cells) was found to be similar to the density on wild-type cells whether the cells were resting or had been activated by treatment with LPS and IL-4. Thus, both mAbs which bind to H2-$A^b$ irrespective of the bound peptides, such as Y3P (FIG. 2A) and M5/114, and mAbs which bind to H2-$A^b$ in a peptide-specific manner, such as BP107 and KH74 stained H2-Oa$^{-/-}$ and H2-Oa$^{++}$ cells equally well. In contrast H2-M-deficient mice were weakly stained by KH74 and not at all by BP107, as has been reported previously (Fung-Leung et al., 1996). The staining with 30-2, a mAb which specifically recognizes CLIP-H2-A$^b$ complexes was very weak on resting wild-type and H2-O$^{-/-}$ B cells, while H2-M$^{-/-}$ B cells were stained well with this antibody. Activation by treatment with LPS and IL-4 increased the 30-2 staining on B cells from all three types of mice, but there was still no difference in staining intensity between wild-type and H2-Oa$^{-/-}$ mice. MAb 15G4 also recognizes CLIP-H2-A$^b$ complexes but with higher affinity than 30-2. The staining with this antibody also showed comparable CLIP-H2-A$^b$ levels on lymph node cells from wild-type and H2-Oa$^{-/-}$ mice, whether the cells were resting or had been activated, while the staining on cells from H2-M$^{-/-}$ mice was very intense. The staining increased on cells from all three types of mice after activation (FIG. 2A).

Immunohistochemistry

Cryostat sections were stained for H2-O or H2-M with rabbit antisera against the H2-Ob tail (K535) or against H2-M (K553) (Karlsson et al., 1994), respectively, followed by biotinylated anti-rabbit IgG (Jackson ImmunoResearch). Bound antibodies were detected with alkaline phosphatase-conjugated streptavidin (Jackson ImmunoResearch) and visualized with colorimetric substrate as described (Surh et al., 1992).

Figure 2B:
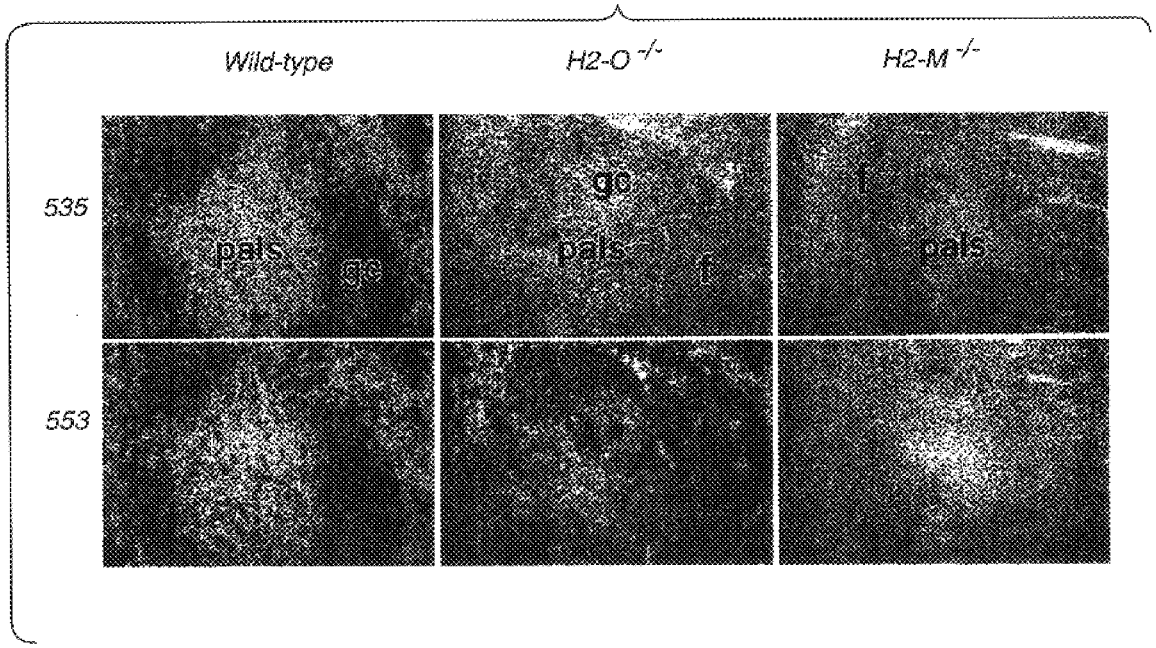

Immunohistochemical analysis of the spleen and lymph node from H2-Oa$^{-/-}$ mice with an antiserum against H2-Ob confirmed the absence of H2-O expression, which in wild type mice is limited mostly to B cells (FIG. 2B) (Karlsson et al., 1991; Wake and Flavell, 1985). As expected from biochemical data (Liljedahl et al., 1996), H2-O was undetectable in the spleen and lymph node of H2-M$^{-/-}$ mice, while H2-M expression was normal in H2-Oa$^{-/-}$ mice (FIG. 2B). Unexpectedly, however, the H2-Ob-specific antiserum gave staining patterns identical to wild-type mice (Karlsson et al., 1991; Surh et al., 1992) on thymic sections from both H2-Oa$^{-/-}$ and H2-M$^{-/-}$ mice; strong staining was observed on medullary epithelial cells with weaker staining on cortical epithelial cells (Surh et al., 1992). The stainings were specific as binding of the antibodies were blocked in the presence of the H2-Ob peptide used to raise the antiserum. We are presently investigating this finding.

Metabolic Labeling and Immunoprecipitation

Splenocytes were labelled with $^{35}$S-methionine and $^{35}$S-cysteine as indicated before lysis in 1% Triton X-100, PBS and Complete proteinase inhibitor cocktail (Boehringer Mannheim, Germany). H2-O was immunoprecipitated with a rabbit antiserum (K535) against the H2-Ob cytoplasmic tail (Karlsson et al., 1991). H2-A$^b$ was precipitated with M5/114 (Bhattacharya et al., 1981). Immunoprecipitates were harvested with protein A or G-sepharose, washed and re-suspended in isoelectric focusing (IEF) sample buffer (FIG. 1B) (Jones, 1980) or SDS-PAGE sample buffer containing 2% SDS without reduction. Samples were left at room temperature for 20 min., then separated on 7.5–12.5% polyacrylamide gels directly or after NEPHGE (pH 3.5–10). Gels were fixed, dried and autoradiographed. Autoradiographs were scanned using an Agfa Arcus II scanner. Composites were printed on a Kodak XLS 8600 printer.

Under mildly denaturing conditions, H2-A$^b$ molecules from both wild-type and H2-M-deficient mice migrate as dimers in SDS-PAGE gels (Fung-Leung et al., 1996; Martin et al., 1996; Miyazaki et al., 1996). The migration of the dimers is not identical, however, and the fact that H$_2$-A$^b$ molecules from H2-M-deficient mice are almost exclusively loaded with CLIP peptide explains this phenomenon. Analysis of H2-A$^b$ molecules immunoprecipitated from metabolically labelled H2-Oa$^{+/+}$ or H2-Oa$^{-/-}$ splenocytes using mAb M5/114 showed that these molecules migrated identically in SDS-PAGE, whether derived from the wild-type or mutant cells, suggesting that the class II molecules in H2-Oa$^{-/-}$ mice contain a mixture of peptides, like the class II molecules from wild-type mice (FIG. 2C).

Immune Functions in the Absence of H2-O

Antigen Presentation Assays

B cells were purified from pooled lymph node and spleen cells by passage over G-10 columns and complement-mediated depletion of T cells by antibodies directed against CD4 (RL 172) and CD8 (3.168) followed by a 90 minute incubation on plastic tissue culture dishes to remove any remaining adherent cells (Webb and Sprent, 1990). Purified B cells (1×10$^5$) were incubated in triplicate overnight with 2×10$^5$ hybridoma cells recognizing sperm whale myoglobin (HMb 4.2.2, kindly provided by Dr. P. Jensen, Emory University, Atlanta, Ga.), hen egg lysozyme (HEL) (BO4) and ribonuclease A (IB-E6) using increasing amounts of relevant antigen or HEL peptide (amino acids 74–91). Recombinant sperm whale myoglobin (Sigma), hen egg lysosyme and ribonuclease A (Calbiochem) were purchased. Cultured hybridoma supernatants were tested for the presence of interleukin-2 (IL-2) using ELISA according to the manufacturer (Genzyme).

Receptor-mediated uptake and presentation to the panel of hybridomas was studied after a 1 hour pulse with phosphorylcholine-conjugated antigens (Gearhart et al., 1975), to B cells purified from 207-4 anti-phosphorylcholine transgenic H2-O$^{+/+}$ or H2-O$^{-/-}$ mice followed by extensive washing. Data are shown in FIG. 3 as mean values ±SD when indicated. The student's t-test was used to determine levels of significance between sample means using Sigma plot 3.0 (Jandel). None of the antigens are presented by APCs from H2-M$^{-/-}$ mice (Martin et al., 1996).

The proportions of B cells as well as of CD4$^+$ and CD8$^+$ T cells in the lymph node, spleen and thymus were similar in H2-Oa-deficient and wild-type mice. Lymph node CD4$^+$ T cells, which displayed a naive phenotype when analyzed by CD44 and CD45RB, reacted normally against allogenic stimulator cells. Likewise we have been unable to find significant differences in the ability of T depleted spleen cells from mutant or wild-type mice to stimulate alloresponses. This finding is not unexpected, since dendritic cells, which express little no H2-O, are thought to be the main cell type mediating the response in this assay (Sprent, 1995). B cells had normal surface expression of IgM, IgD, CD5, CD16, CD19, CD22, CD23, CD45R and HSA.

Figure 3A:
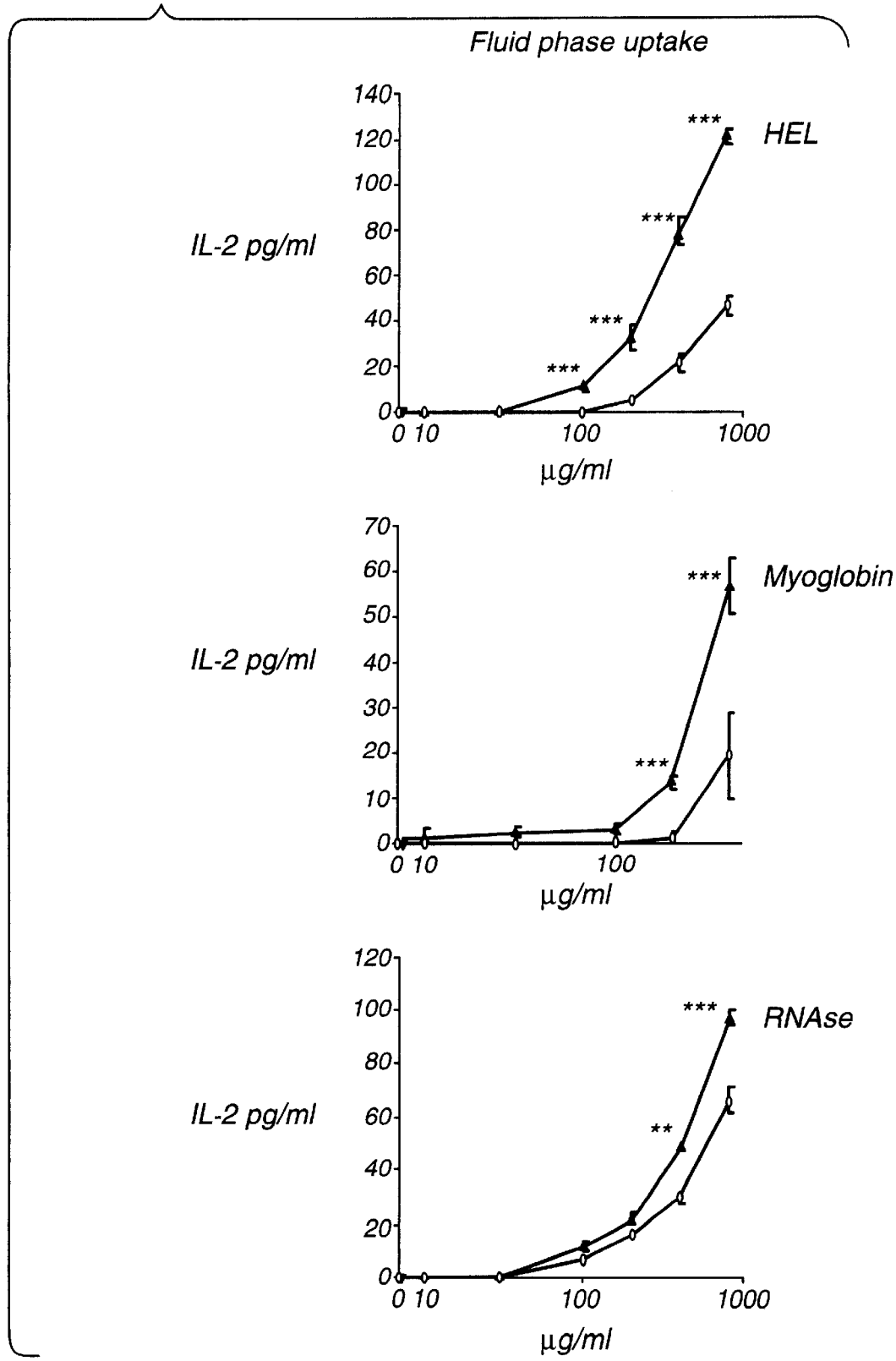
Figure 3B:
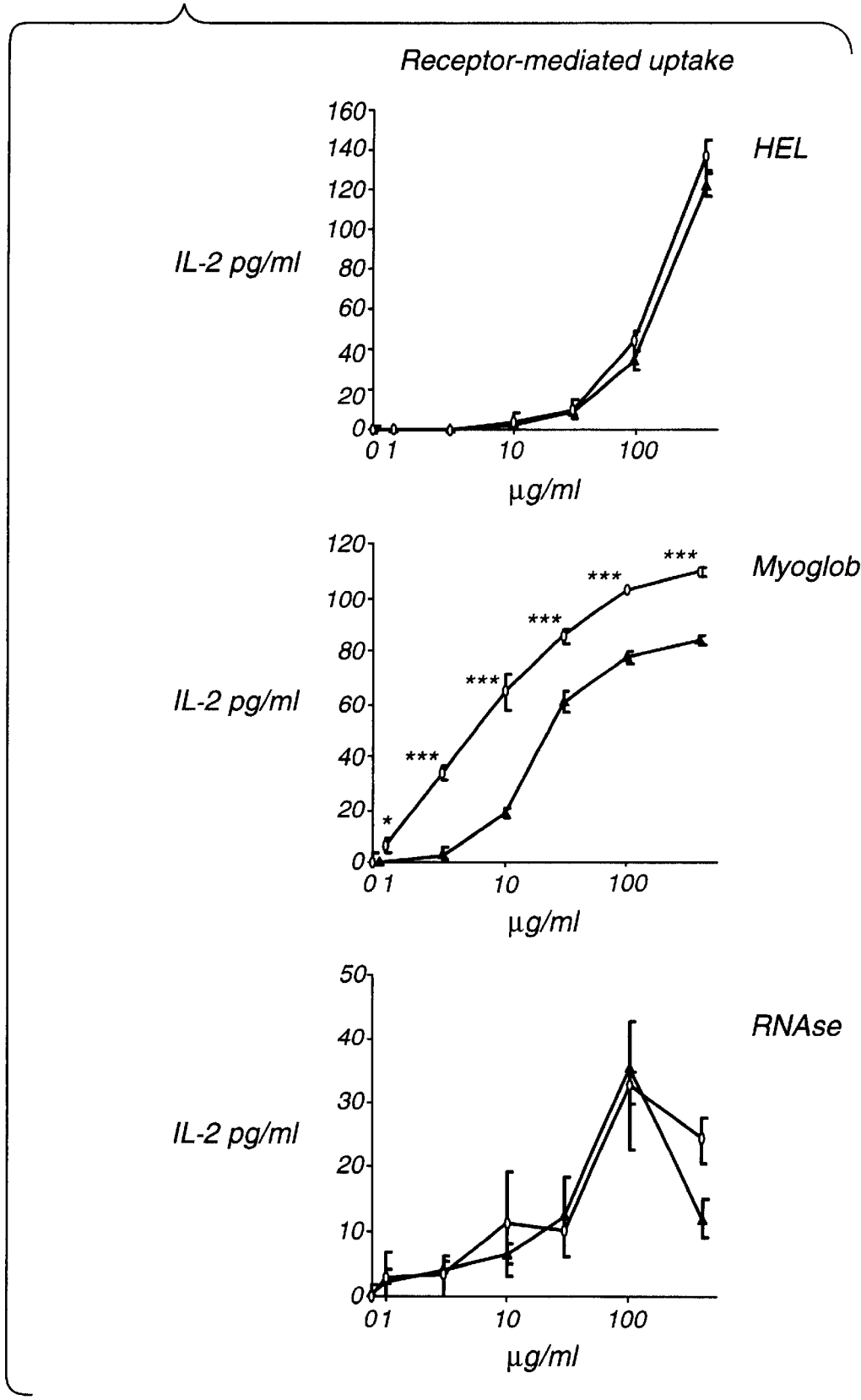
Figure 3C:
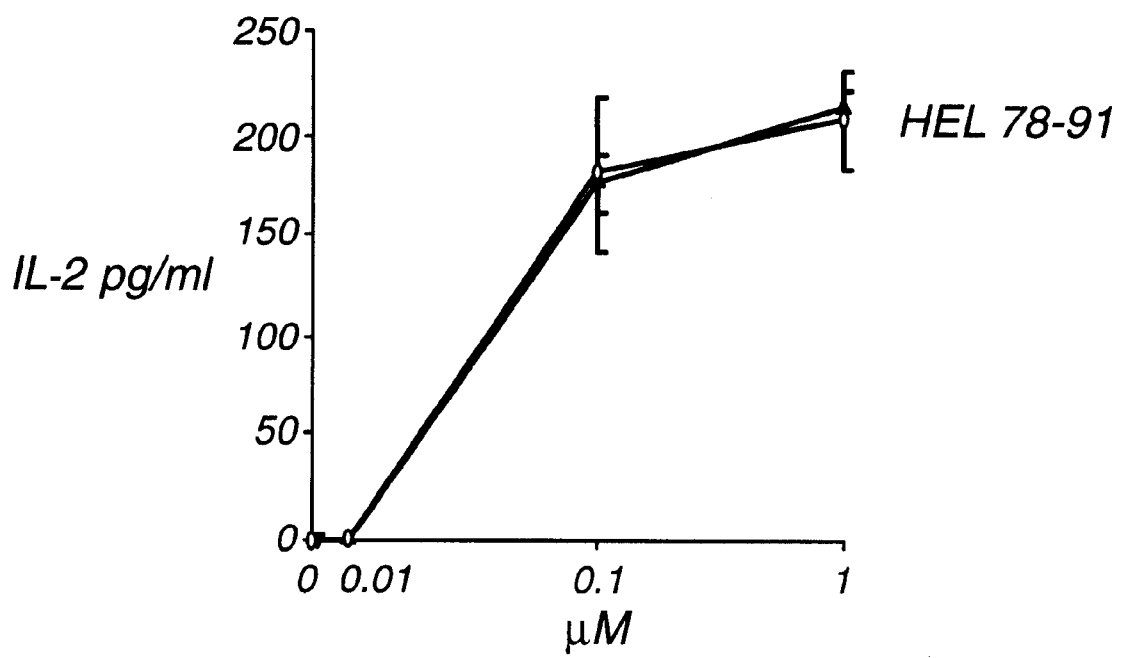

To determine the capacity of B cells from H2-Oa$^{-/-}$ mice to process and present protein antigens, B cells from wild-type and mutant mice were used to stimulate IL-2 production from a panel of T cell hybridomas reactive with different antigens. FIG. 3A shows that while all the antigens could be presented by the wild-type cells to some extent after overnight incubation with the antigen, hen egg lysozyme (HEL) and sperm whale myoglobin were distinctly better presented by the H2-Oa$^{-/-}$ B cells, while the difference for RNAse was smaller (but consistently seen in a number of experiments). To evaluate whether also antigens internalized by membrane immunoglobulin (mIg) were differentially presented, H2-Oa$^{-/-}$ or wild-type litter-mates were bred with 207-4 mice, carrying transgenes for phosphorylcholine (pc)-specific immunoglobulin $\mu$ and k chains. B cells from these mice were pulsed for 60 minutes with pc-conjugated antigens and analyzed for their ability to stimulate the same panel of hybridomas as above. In this situation, the presentation of myoglobin by wild-type cells was superior to the presentation by the H2-Oa$^{-/-}$-deficient cells, while HEL and RNAse were presented equally well by the two types of presenting cells (FIG. 3B). There was no difference in the presentation between un-conjugated and pc-conjugated antigens when tested after fluid-phase uptake. B cells from mutant or wild-type mice were equally efficient at presenting HEL peptide 74–91 to the HEL-reactive hybridoma (FIG. 3C).

The increased presentation of antigens internalized by fluid-phase endocytosis could potentially lead to less stringent requirements for delivery of T cell help and thus for the expansion of B cells. An indication that this may be the case was obtained when the serum levels of immunoglobulins were analyzed in non-immunized (non-transgenic) mice. While young H2-Oa-deficient and wild-type animals (6 weeks of age) had similar immunoglobulin levels of all subclasses, older H2-Oa-deficient mice (10 months of age) had distinctly increased levels of IgGl compared to the wild-type controls (FIG. 4). Other IgG subclasses and IgA did not show significant differences between the two types of mice.

Analysis of DM-DO Interaction in Vitro
Recombinant Proteins cDNAs were modified by PCR The transmembrane domain was deleted in DRA and DRB1; the transmembrane and cytoplasmic tails of DMA and DMB were replaced by six histidines followed by a stop codon. DO was expressed as a fusion protein where the transmembrane and cytoplasmic tails of DOA and DOB were replaced by human IgGl Fc domains. CD27Fc has been described (Ozaki et al., 1997) Constructs were cloned into expression vector pRMHa-3 and expressed in Drosophila melanogaster-derived Schneider-2 cells (Matsumura et al., 1992). Soluble proteins were purified from the culture medium using affinity chromatography followed by gel filtration. For the initial purification step a monoclonal antibody LB3.1 column was used for DR1 as described (Stern and Wiley, 1992), Ni-NTA agarose columns for DM and DMDO complexes and protein A sepharose columns for DO and CD27Fc. Superdex 200 columns (Pharmacia) were used for gel filtration. DMDO complexes were digested with immobilised papain (Pierce) according to the manufacturers instructions. Fc domains were removed using protein A sepharose. DMDO complexes were also formed in vitro by incubating DM with 4-fold excess DO for 4 hours at room temperature. Complexes were isolated using Ni-NTA agarose beads. These complexes behaved identically to DMDO complexes isolated from cells expressing both DM and DO. The correct identities of all proteins were confirmed by amino-terminal protein sequencing. DMDO complexes contained equimolar amounts of all four chains. Protein concentrations were determined using BCA (Pierce). Human IgGl was purchased from Sigma.

Peptide Exchange Assays

DR-peptide complexes were formed by incubation of 100 times molar excess of peptide with recombinant DR for 48 hours at pH 6.0. DR-peptide complexes were separated from free peptide by gel filtration using a Superdex 75 column (Pharmacia). Binding reactions were done using DR1 (pre-loaded with non-florescent CLIP 81-104, except as stated) with 5–20 fold excess of peptide at 37° C. in 45 mM HEPES, MES or sodium acetate buffer (depending on pH) with 100 mM NaCl. Reactions were stopped by addition of Tris-HCl pH 8.0 to 600 mM and frozen until analysis. DR-peptide complexes were separated from free peptide by gel filtration over Sephadex G-50 (Pharmacia) columns (2 ml bed volume). Bound fluorescence was measured using either a Shimadzu single sample fluorometer or a Perseptive Cytofluor 96 well fluorometer. Samples were excited at 485 nM and emission was analysed at 530 nM.

The similar levels of CLIP-H2-$A^b$ complexes in both wild-type and mutant mice suggested that H2-O do not effectively inhibit CLIP release in vivo, yet the changed presentation of antigenic epitopes showed that H2-O did influence peptide presentation, either qualitatively or quantitatively. To investigate the molecular basis for this phenomenon recombinant soluble DO, DM and DR molecules as well as DMDO complexes were produced in insect cells (Jackson et al., 1992; Matsumura et al., 1992). Human molecules rather than mouse molecules were chosen since DM function in vitro has been better characterized in the human system (Denzin and Cresswell, 1995; Kropshofer et al., 1997; Sloan et al., 1995; Weber et al., 1996). Both transmembrane and truncated soluble forms of DO are unstable in the absence of DM and only minor amounts of DO exits the ER (Liljedahl et al., 1996 and FIG. 1B and C) To overcome this problem we fused the extracellular domains of DOA and DOB to the Fc domain of human IgGl, thus creating a DO-Fc fusion protein (below called DO). DMDO complexes were isolated from cells expressing all four DM and DO chains. Soluble DM and DR molecules were generated as described in the Materials and Methods section. The activity of the recombinant DM and DMDO molecules was tested for their ability to promote peptide loading of a fluorescent peptide from hemagglutinin (amino acids 306–318; HA) to DR1. At pH 5.5 the activity of the recombinant molecules was found to be very similar to what has been described for affinity purified molecules from B cells (Denzin et al., 1997), confirming that DO has an inhibitory effect on DM function (FIG. 5A). DM can release other peptides than CLIP from class II molecules (Kropshofer et al., 1997; Weber et al., 1996) and the changed antigen presentation in the H2-Oa$^{-/-}$ mice could be a reflection of changed specificity for peptide release of the H2-M-H2-O complexes compared with H2-M alone. We have analyzed the release of several different peptides from DR1 in vitro (shown for CLIP and HA in FIG. 5B and C), but have not been able to find any differences in specificity between DMDO and DM. In contrast, at pH 5.5 DMDO complexes consistently appear to release peptides with slower kinetics than DM alone.

DO is a pH-dependent Inhibitor of DM Function
ANS Fluorescence 200 nM of the indicated proteins were incubated in buffer (20 mM HEPES, MES or sodium acetate). ANS was added to a final of 20 µM either immediately or after 4 hours of incubation. After ANS addition, samples were excited at 372 nm and emission was analysed at 480 nm. Samples were neutralized by the addition of HEPES pH 7.4 to 100 mM as indicated. Emission spectra (410–600 nm) were also analysed, but the wavelength of fluorescence maximum did not substantially shift upon acidification.

Figure 6B:
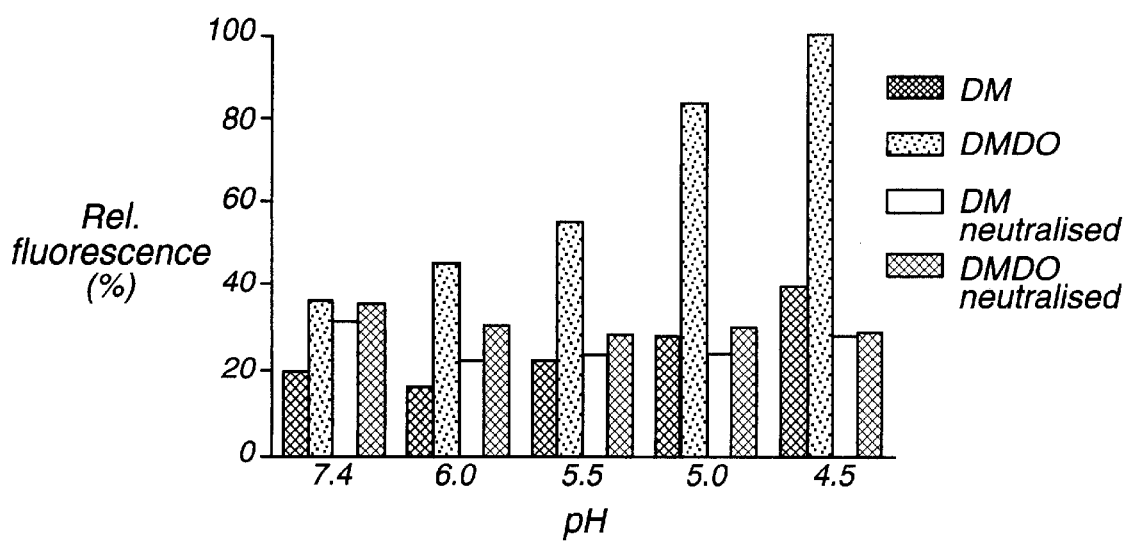

Alterations in pH often result in changed protein conformation and changed protein function. To investigate whether structural changes occurred in the purified proteins during acidification, we used the fluorescent probe ANS (1-anilinonaphtalene-8-sulphonic acid). ANS fluorescence is low in aqueous solutions, but strongly increased when the probe becomes associated with exposed hydrophobic protein surfaces (Boniface et al., 1996; Runnels et al., 1996; Stryer, 1968). While the ANS fluorescence in samples containing DM alone did not increase significantly upon acidification (FIG. 6A), the fluorescence in DO and DMDO-containing samples increased drastically, suggesting a change in DO conformation at lower pH. However, though DO may contribute most of the conformation change in the DMDO complexes, it can not be excluded that the conformation of the associated DM molecules is also altered. The conformation change in DO-containing samples was independent of the DO Fc domain since the fluorescence of CD27Fc did not increase at acidic pH. Incubation of DM or DMDO complexes at the indicated pH for 4 hours did not further increase the ANS fluorescence (FIG. 6B). Neutralization of the samples containing DO restored the original level of fluorescence, suggesting that the conformational changes were reversible.

Figure 7A:
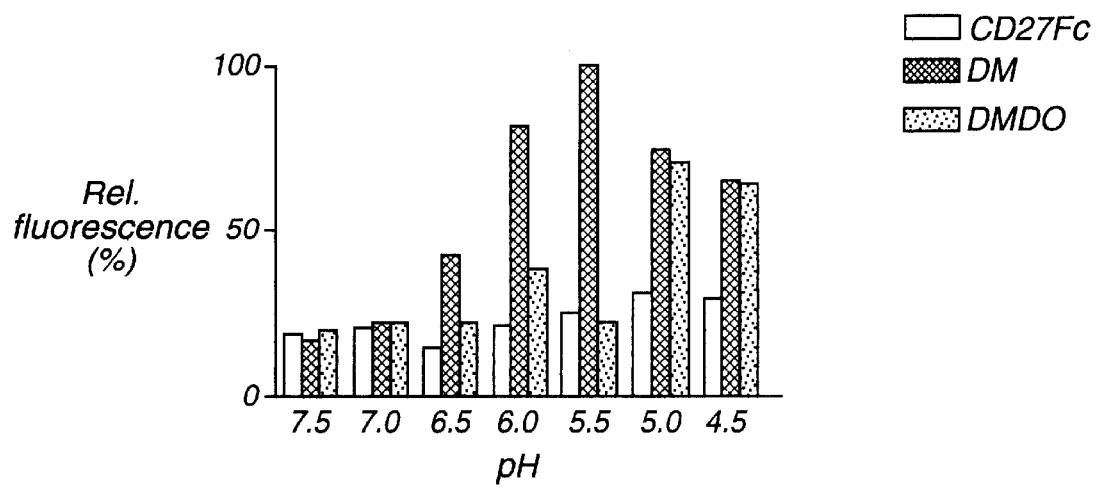

DM is efficient in the pH range between 6 and 4.5 (though the optimal pH for peptide loading to class II molecules is peptide and haplotype dependent) (Denzin and Cresswell, 1995; Jensen, 1991; Sherman et al., 1995; Sloan et al., 1995). To determine whether the conformational change in DO correlated with the capacity for peptide exchange of DMDO complexes, peptide binding to DR1 was analyzed at different pH in the presence of equimolar amounts of DM or DMDO. While DM was found to catalyze loading of HA peptide to DR1 throughout the expected pH range (in this case with optimal loading at pH 5.5), DMDO complexes were inactive at higher pH, but promoted peptide loading almost as well as DM at pH 4.5 (FIG. 7A). A similarly increased activity of the DMDO complex at pH 4.5 compared to pH 5.5 was seen for the loading of HLA-A2 peptide to DR1 and (to a smaller extent) for the association of a peptide from a mycobacterial heat shock protein (HSP 65) to DR3).

Figure 7B:
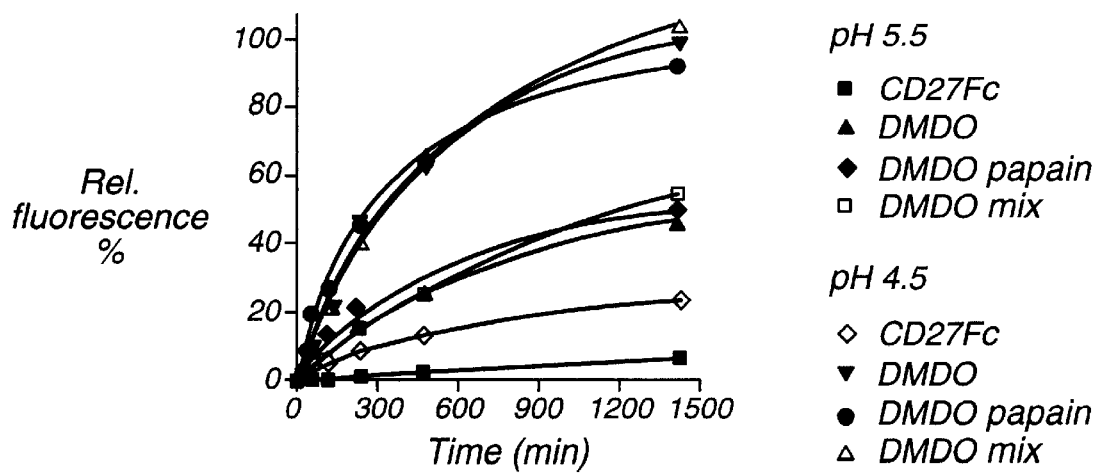
Figure 7C:
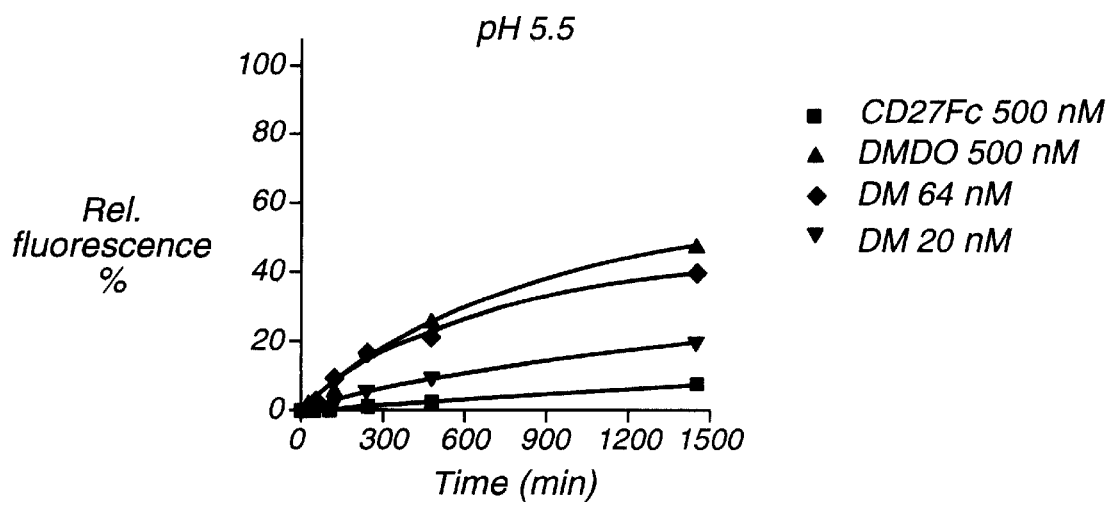
Figure 7D:
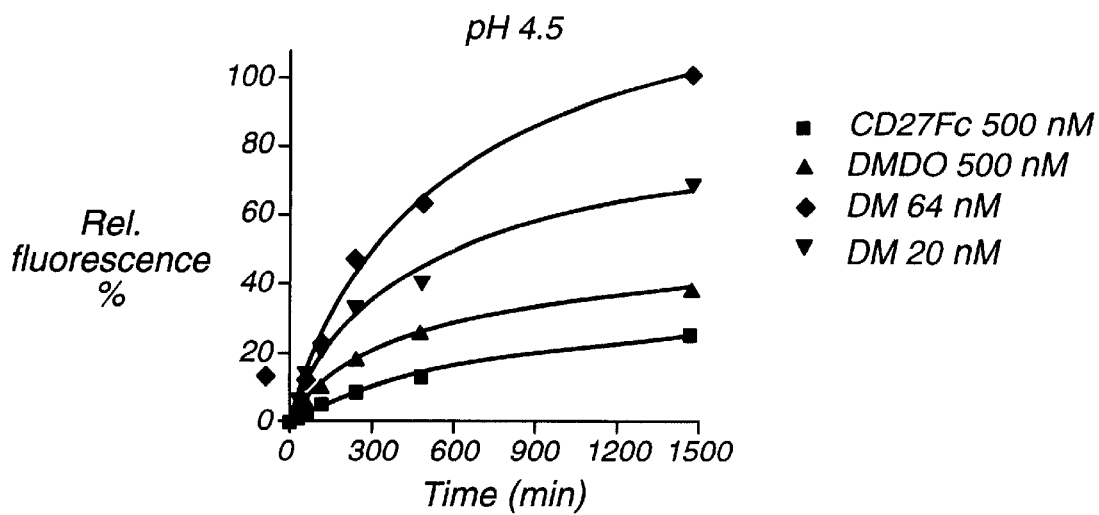

To exclude the possibility that the Fc domain of DO was influencing the function of the DMDO complexes, this domain was removed by papain digestion and the capacity of the modified complex to catalyze peptide loading was analyzed. FIG. 7B shows that the papain-digested complexes, as well as DMDO complexes formed in vitro from free DM and DO (=DMDO Mix) promoted peptide loading with similar kinetics as the in-vivo-formed DMDO complexes, both at pH 5.5 and at pH 4.5.

At equilibrium, a certain amount of free DM is present in the DMDO complex preparation (since the interaction is non-covalent). To ascertain that the pool of free DM present at neutral pH was not sufficient to mediate the peptide loading we detected with the DMDO complexes (if for example the DMDO complexes were irreversibly destroyed), binding experiments were done at pH 5.5 and at pH 4.5 using DMDO complexes and two concentrations of DM. Comparison of the loading kinetics showed that while the higher concentration of DM (64 nM) was almost as effective as DMDO at pH 5.5 (FIG. 7C), DMDO was distinctly better at the lower pH (FIG. 7D), suggesting either a release of more free active DM from the DMDO complexes upon acidification, or a change in the DMDO complex that increased catalytic function at the lower pH.

$H2-O^{-/-}$ Mice Produce a Substantially Greater Frequency of High Affinity Antibodies that $H2-O^{+/+}$ Mice The affinity maturation of the antigen-specific IgG1 response against T dependent antigens (nitrophenol (NP-) conjugated ovalbumin) was found to be increased in the mice lacking H2-O when compared to the H2-O expressing control mice.

Groups of wild-type (w.t.) i.e. H2-O expressing or $H2-O^{-/-}$ mice of 6–8 weeks of age were immunized i.p. with 1 g or 100 g ovalbumin conjugated with nitrophenol (NP-OVA). Mice immunized with 1 g of antigen were boosted on day 22 with 1 g NP-OVA i.p. Mice were bled by eye bleeding as indicated in Fig X and the resulting sera were tested in ELISA assays for reactivity against NP conjugated to bovine serum albumin (BSA) either at a low conjugation ratio of 2.5 NP per BSA molecule (NP-BSA 2.5) to detect high affinity IgG1 antibodies or at a high conjugation ratio of 23 NP per BSA molecule (NP-BSA 23) to detect both high and low affinity IgG1 antibodies. The reactivities of the antisera were converted to arbitrary units by comparison with an antiserum from a mouse hyperimmunized with NP-OVA. The relative reactivities of high affinity and total antibodies are plotted as the ratio between NP2.5 and NP23 reactivity in the sera from the different mice. The presented data show that H2-O-/- mice produce significantly higher levels of high affinity antibodies in response to T cell dependent antigens than do H2-O+/+ mice.

Improved affinity maturation of the antibody response in H2-O-/- mice is shown in FIGS. 8 and 9. The ratio of high affinity IgG1 (measured by the binding to NP-BSA-2.5) to the total amount of antigen-specific IgG1 (measured by the binding to NP-BSA-23) after low dose immunization with NP-OVA is shown in FIG. 8. FIG. 9 shows the ratio of high affinity IgG1 (measured by the binding to NP-BSA-2.5) to the total amount of antigen-specific IgG1(measured by the binding to NP-BSA-23) with high dose immunization (FIG. 9) with NP-OVA. Antisera from 10 mice per group (i.e. 10 wild-type mice expressing H2-O (w.t., left) or 10 H2-O-/- mice (H2-O-/-, right) were examined at the indicated days after immunization and the response of the individual mice is indicated in the figure with closed circles. In the case of the low dose immunization, "primary" corresponds to the response after the first immunization, "secondary" to the response after the boosting at day 22 after the initial immunization. The means of the different groups is indicated by horizontal bars.

The data shown in FIGS. 8 and 9 demonstrate that H2-O-/- mice are useful for the generation of high affinity antisera against different antigens and that the H2-O-/- mice are useful for the generation of monoclonal antibody producing B cell hybridomas after immunization of the mice.

REFERENCES

Accolla, R. S., Cina, R., Montesoro, E., and Celada, F. (1981). Antibody-mediated activation of genetically defective Escherichia coli beta-galactosidases by monoclonal antibodies produced by somatic cell hybrids. Proc Natl Acad Sci U S A 78, 2478–82.

Albert, L. J., Ghumman, B., and Watts, T. H. (1996). Effect of HLA-DM transfection on hen egg lysozyme presentation by T2.Ak cells. J. Immunol. 157, 2247–2255.

Amigorena, S., Drake, J. R., Webster, P., and Mellman, I. (1994). Transient accumulation of new class II MHC molecules in a novel endocytic compartment in B lymphocytes. Nature 369, 113–20.

Bhattacharya, A., Dorf, M. E., and Springer, T. A. (1981). A shared alloantigenic determinant on Ia antigens encoded by the I-A and I-E subregions: evidence for I region gene duplication. J. Immunol. 127, 2488–95.

Boniface, J. J., Lyons, D. S., Wettstein, D. A., Allbritton, N. L., and Davis, M. M. (1996). Evidence for a conformational change in a class II major histocompatibility complex molecule occurring in the same pH range where antigen binding is enhanced. J Exp Med 183, 119–26.

Calafat, J., Nijenhuis, M., Janssen, H., Tulp, A., Dusseljee, S., Wubbolts, R., and Neefjes, J. (1994). Major histocompatibility complex class II molecules induce the formation of endocytic MIIC-like structures. J. Cell Biol. 126, 967–77.

Cella, M., Sallusto, F., and Lanzavecchia, A. (1997). Origin, maturation and antigen presenting function of dendritic cells. Curr Opin Immunol 9, 10–6.

Denzin, L. K., and Cresswell, P. (1995). HLA-DM induces CLIP dissociation from MHC class II alpha beta dimers and facilitates peptide loading. Cell 82, 155–65.

Denzin, L. K., Robbins, N. F., Carboy-Newcomb, C., and Cresswell, P. (1994). Assembly and intracellular transport of HLA-DM and correction of the class II antigen-processing defect in T2 cells. Immunity 1, 595–606.

Denzin, L. K., Sant'Angelo, D. B., Hammond, C., Surman, M. J., and Cresswell, P. (1997). Negative regulation by HLA-DO of MHC class II-restricted antigen processing. Science 278, 106–109.

Douek, D. C., and Altmann, D. M. (1997). HLA-DO is an intracellular class II molecule with distinctive thymic expression. Int Immunol 9, 355–364.

Fling, S. P., Arp, B., and Pious, D. (1994). HLA-DMA and -DMB genes are both required for MHC class II/peptide complex formation in antigen-presenting cells. Nature 368, 554–558.

Fung-Leung, W.-P., Surh, C. D., Liljedahl, M., Pang, J., Leturcq, D., Peterson, P. A., Webb, S. R., and Karlsson, L. (1996). Antigen presentation and T cell development in H2-M deficient mice. Science 271, 1278–1281.

Gearhart, P. J., Sigal, N. H., and Klinman, N. R. (1975). Heterogeneity of the BALB/c antiphosphorylcholine antibody response at the precursor cell level. J Exp Med 141, 56–71.

Jackson, M. R., Song, E. S., Yang, Y., and Peterson, P. A. (1992). Empty and peptide-containing conformers of class I major histocompatibility complex molecules expressed in Drosophila melanogaster cells. Proc. Natl. Acad. Sci. U.S.A. 89, 12117–21.

Jemmerson, R., and Paterson, Y. (1986). Mapping epitopes on a protein antigen by the proteolysis of antigen- antibody complexes. Science 232, 1001–4.

Jensen, P. E. (1991). Enhanced binding of peptide antigen to purified class II major histocompatibility glycoproteins at acidic pH. J. Exp. Med. 174, 1111–20.

Jones, P. P. (1980). Analysis of Radiolabeled Lymphocyte Proteins by One- and Two-Dimensional Gel Electrophoresis. In Selected methods in Cellular Immunology, B. P. Mishell, and Shigii, S. P., ed. (San Fransisco: Freeman), pp. 398–440.

Karlsson, L., Peleraux, A., Lindstedt, R., Liljedahl, M., and Peterson, P. A. (1994). Reconstitution of an operational MHC class II compartment in nonantigen-presenting cells. Science 266, 1569–1573.

Karlsson, L., Surh, C. D., Sprent, J., and Peterson, P. A. (1991). A novel class II MHC molecule with unusual tissue distribution. Nature 351, 485–488.

Kleijmeer, M. J., Oorschot, V. M., and Geuze, H. J. (1994). Human resident langerhans cells display a lysosomal compartment enriched in MHC class II. J. Invest. Dermatol. 103, 516–523.

Kropshofer, H., Arndt, S. O., Moldenhauer, G., Hammerling, G. J., and Vogt, A. B. (1997). HLA-DM acts as a molecular chaperone and rescues empty HLA-DR molecules at lysosomal pH. Immunity 6, 293–302.

Kropshofer, H., Hammerling, G. J., and Vogt, A. B. (1997). How HLA-DM edits the MHC class II peptide repertoire: survival of the fittest? Immunol. Today 18, 77–82.

Lanzavecchia, A. (1985). Antigen-specific interaction between T and B cells. Nature 314, 537–539.

Liljedahl, M., Kuwana, T., Fung-Leung W.-P., Jackson, M. R., Peterson, P. A. and Karlsson, L. (1996). HLA-DO is a lysosomal resident which requires association with HLA-DM for efficient intracellular transport. EMBO J. 15, 4817–4824.

Martin, W. D., Hicks, G. G., Mendiratta, S. K., Leva, H. I., Ruley, H. E., and Van Kaer, L. (1996). H2-M Mutant Mice Are Defective in the Peptide Loading of Class II Molecules, Antigen Presentation, and T Cell Repertoire Selection. Cell 84, 543–550.

Matsumura, M., Saito, Y., Jackson, M. R., Song, E. S., and Peterson, P. A. (1992). In vitro peptide binding to soluble empty class I major histocompatibility complex molecules isolated from transfected Drosophila melanogaster cells. J. Biol. Chem. 267, 23589–23595.

Mellins, E., Smith, L., Arp, B., Cotner, T., Celis, E., and Pious, D. (1990). Defective processing and presentation of exogenous antigens in mutants with normal HLA class II genes. Nature 343, 71–4.

Mitchell, R. N., Barnes, K. A., Grupp, S. A., Sanchez, M., Misulovin, Z., Nussenzweig, M. C., and Abbas, A. K. (1995). Intracellular targeting of antigens internalized by membrane immunoglobulin in B lymphocytes. J. Exp. Med. 181, 1705–14.

Miyazaki, T., Wolf, P., Tourne, S., Waltzinger, C., Dierich, A., Barois, N., Ploegh, H., Benoist, C., and Mathis, D. (1996). Mice Lacking H2-M Complexes, Enigmatic Elements of the MHC Class II Peptide-Loading Pathway. Cell 84, 531–541.

Morris, P., Shaman, J., Attaya, M., Amaya, M., Goodman, S., Bergman, C., Monaco, J. J., and Mellins, E. (1994). An essential role for HLA-DM in antigen presentation by class II major histocompatibility molecules. Nature 368, 551–4.

Ozaki, M. E., Karlsson, L., Peterson, P. A., and Webb, S. R. (1997). Antigen specificity of dual reactive T hybridomas determines the requirement for CD40 ligand-CD40 interactions. J Immunol 159, 214–21.

Peters, P. J., Neefjes, J. J., Oorschot, V., Ploegh, H. L., and Geuze, H. J. (1991). Segregation of MHC class II molecules from MHC class I molecules in the Golgi complex for transport to lysosomal compartments . Nature 349, 669–676.

Rock, K. L., Benacerraf, B., and Abbas, A. K. (1984). Antigen presentation by hapten-specific B lymphocytes. I. Role of surface immunoglobulin receptors. J. Exp. Med. 160, 1102–1113.

Runnels, H. A., Moore, J. C., and Jensen, P. E. (1996). A structural transition in class II major histocompatibility complex proteins at mildly acidic pH. J Exp Med 183, 127–36.

Sanderson, F., Kleijmeer, M. J., Kelly, A., Verwoerd, D., Tulp, A., Neefjes, J. J., Geuze, H. J., and Trowsdale, J. (1994). Accumulation of HLA-DM, a regulator of antigen presentation, in MHC class II compartments. Science 266, 1566–1569.

Sherman, M. A., Weber, D. A., and Jensen, P. E. (1995). DM enhances peptide binding to class II MHC by release of invariant chain-derived peptide. Immunity 3, 197–205.

Simitsek, P. D., Campbell, D. G., Lanzavecchia, A., Fairweather, N., and Watts, C. (1995). Modulation of antigen processing by bound antibodies can boost or suppress class II major histocompatibility complex presentation of different T cell determinants. J. Exp. Med. 181, 1957–1963.

Sloan, V. S., Cameron, P., Porter, G., Gammon, M., Amaya, M., Mellins, E., and Zaller, D. M. (1995). Mediation by HLA-DM of dissociation of peptides from HLA-DR. Nature 375, 802–806.

Sprent, J. (1995). Antigen-presenting cells. Professionals and amateurs. Curr Biol 5, 1095–7.

Stern, L. J., and Wiley, D. C. (1992). The human class II MHC protein HLA-DR1 assembles as empty alpha beta heterodimers in the absence of antigenic peptide. Cell 68, 465–77.

Storb, U., Pinkert, C., Arp, B., Engler, P., Gollahon, K., Manz, J., Brady, W., and Brinster, R. L. (1986). Transgenic mice with mu and kappa genes encoding antiphosphorylcholine antibodies. J Exp Med 164, 627–41.

Stryer, L. (1968). Fluorescence spectroscopy of proteins. Science 162, 526–33.

Surh, C. D., Gao, E. K., Kosaka, H., Lo, D., Ahn, C., Murphy, D. B., Karlsson, L., Peterson, P., and Sprent, J. (1992). Two subsets of epithelial cells in the thymic medulla. J. Exp. Med. 176, 495–505.

Tonelle, C., DeMars, R., and Long, E. O. (1985). DOb: A new b chain gene in HLA-D with a distinct regulation of expression. EMBO J. 4, 2839–2847.

Tulp, A., Verwoerd, D., Dobberstein, B., Ploegh, H. L., and Pieters, J. (1994). Isolation and characterization of the intracellular MHC class II compartment. Nature 369, 120–126.

Vitetta, E. S., Berton, M. T., Burger, C., Kepron, M., Lee, W. T., and Yin, X. M. (1991). Memory B and T cells. Annu. Rev. Immunol., 193–217.

Wake, C. T., and Flavell, R. A. (1985). Multiple mechanisms regulate the expression of murine immune response genes. Cell 42, 623–8.

Watts, C. (1997). Capture and processing of exogenous antigens for presentation on MHC molecules. Annu. Rev. Immunol. 15, 821–850.

Webb, S. R., and Sprent, J. (1990). Induction of Neonatal Tolerance to Mls$^a$ Antigens by CD8+ T Cells. Science 248, 1643–1646.

Weber, D. A., Evavold, B. D., and Jensen, P. E. (1996). Enhanced dissociation of HLA-DR-bound peptides in the presence of HLA-DM. Science 274, 618–620.

West, M. A., Lucocq, J. M., and Watts, C. (1994). Antigen processing and class II MHC peptide-loading compartments in human B-lymphoblastoid cells. Nature 369, 147–151.

Wolf, P. R., and Ploegh, H. L. (1995). How MHC class II molecules acquire peptide cargo: Biosynthesis and trafficking through the endocytic pathway. Ann. Rev. Cell Dev. Biol. 11, 267–306.

What is claimed is:

1. A method for the production of B-cells specific for an antigen, comprising:

a) immunizing an H2-O-/- mouse with a sufficient amount of said antigen to produce an immune response thereby producing an immunized mouse; and b) collecting said B-cells from said immunized mouse.

2. A method for the production of antibodies having an affinity for an antigen, comprising:

a) immunizing an H2-O-/- mouse with a sufficient amount of said antigen to cause antibody production thereby producing an immunized mouse; and b) collecting said antibodies from said immunized mouse.

* * * * *